(12) United States Patent
Peterson et al.

(10) Patent No.: US 9,066,845 B2
(45) Date of Patent: *Jun. 30, 2015

(54) ELECTRODE CONFIGURATION FOR AN IMPLANTABLE ELECTROACUPUNCTURE DEVICE

(71) Applicant: Valencia Technologies Corporation, Valencia, CA (US)

(72) Inventors: David K. L. Peterson, Valencia, CA (US); Chuladatta H. Thenuwara, Castaic, CA (US)

(73) Assignee: Valencia Technologies Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/776,155

(22) Filed: Feb. 25, 2013

(65) Prior Publication Data

US 2014/0214144 A1 Jul. 31, 2014

Related U.S. Application Data

(63) Continuation-in-part of application No. 13/598,582, filed on Aug. 29, 2012, now Pat. No. 8,965,511.

(60) Provisional application No. 61/606,995, filed on Mar. 6, 2012, provisional application No. 61/676,275, filed on Jul. 26, 2012.

(51) Int. Cl.
*A61N 1/00* (2006.01)
*A61H 39/00* (2006.01)
*A61N 1/04* (2006.01)

(52) U.S. Cl.
CPC ............... *A61H 39/002* (2013.01); *A61N 1/04* (2013.01)

(58) Field of Classification Search
None
See application file for complete search history.

(56) References Cited

U.S. PATENT DOCUMENTS

| 4,031,899 | A | 6/1977 | Renirie |
| 4,157,720 | A | 6/1979 | Greatbatch |
| 4,345,604 | A | 8/1982 | Renirie |

(Continued)

OTHER PUBLICATIONS

WHO Standard Acupuncture Point Locations in the Western Pacific Region, World Health Organization (WHO), Western Pacific Region, 2008 (updated and reprinted 2009), ISBN 978 92 9061 248 7. The Table of Contents, Forward (v-vi), General Guidelines for Acupuncture Point Locations (1-21), as well as pp. 33, 35, 39, 45, 64, 151, 154, 171, 188 and 197.

(Continued)

*Primary Examiner* — Christopher D Koharski
*Assistant Examiner* — Elizabeth K So
(74) *Attorney, Agent, or Firm* — Bryant R. Gold

(57) ABSTRACT

An implantable electroacupuncture device (IEAD) treats a disease or medical condition of a patient through application of stimulation pulses applied at a specified acupoint or other target tissue location at a very low duty cycle. In a preferred implementation, the IEAD is an implantable, coin-sized, self-contained, leadless device having at least two electrodes attached to an outside surface of its housing, with at least one electrode on the top or bottom surface of the housing functioning as a cathode, and at least one electrode on the perimeter edge of the housing functioning as an anode. The electrodes may be segmented to include an array of smaller cathodic or anodic electrodes, each of which may be selectively turned ON or OFF so as to provide a convenient mechanism for adjusting the density of the stimulus current flowing through the cathodic electrode surface area.

8 Claims, 23 Drawing Sheets

(56) References Cited

U.S. PATENT DOCUMENTS

| | | | |
|---|---|---|---|
| 4,528,072 | A | 7/1985 | Kurosawa |
| 4,535,784 | A | 8/1985 | Rohlicek |
| 4,566,064 | A | 1/1986 | Whitaker |
| 5,195,517 | A | 3/1993 | Chen |
| 5,199,428 | A | 4/1993 | Obel |
| 5,211,175 | A | 5/1993 | Gleason |
| 5,250,068 | A | 10/1993 | Ideguchi |
| 5,251,637 | A | 10/1993 | Shalvi |
| 5,372,605 | A | 12/1994 | Adams |
| 5,544,656 | A | 8/1996 | Pitsillides |
| 5,707,400 | A | 1/1998 | Terry, Jr. |
| 5,891,181 | A | 4/1999 | Zhu |
| 6,006,134 | A | 12/1999 | Hill |
| 6,178,352 | B1 | 1/2001 | Gruzdowich |
| 6,393,324 | B2 | 5/2002 | Gruzdowich |
| 6,522,926 | B1 | 2/2003 | Kieval |
| 6,658,298 | B2 | 12/2003 | Gruzdowich |
| 6,735,475 | B1 | 5/2004 | Whitehurst |
| 6,839,596 | B2 | 1/2005 | Nelson |
| 6,950,707 | B2 | 9/2005 | Whitehurst |
| 6,978,174 | B2 | 12/2005 | Gelfand |
| 7,003,352 | B1 | 2/2006 | Whitehurst |
| 7,013,177 | B1 | 3/2006 | Whitehurst |
| 7,046,499 | B1 | 5/2006 | Imani |
| 7,136,701 | B2 | 11/2006 | Greatbatch |
| 7,155,279 | B2 | 12/2006 | Whitehurst |
| 7,162,303 | B2 | 1/2007 | Levin |
| 7,171,266 | B2 | 1/2007 | Gruzdowich |
| 7,203,548 | B2 | 4/2007 | Whitehurst |
| 7,292,890 | B2 | 11/2007 | Whitehurst |
| 7,321,792 | B1 | 1/2008 | Min et al. |
| 7,373,204 | B2 | 5/2008 | Gelfand |
| 7,440,806 | B1 | 10/2008 | Whitehurst |
| 7,610,100 | B2 | 10/2009 | Jaax |
| 7,620,451 | B2 | 11/2009 | Demarais |
| 7,657,316 | B2 | 2/2010 | Jaax |
| 7,962,219 | B2 | 6/2011 | Jaax |
| 2003/0078642 | A1 | 4/2003 | Malaney |
| 2003/0158588 | A1* | 8/2003 | Rizzo et al. ............... 607/54 |
| 2003/0187485 | A1 | 10/2003 | Sturman |
| 2003/0195583 | A1 | 10/2003 | Gruzdowich |
| 2005/0107832 | A1 | 5/2005 | Bernabei |
| 2005/0228460 | A1 | 10/2005 | Levin |
| 2005/0234533 | A1 | 10/2005 | Schulman |
| 2006/0041283 | A1 | 2/2006 | Gelfand |
| 2007/0005119 | A1 | 1/2007 | Crohn |
| 2007/0219595 | A1 | 9/2007 | He |
| 2007/0255319 | A1* | 11/2007 | Greenberg et al. .......... 607/2 |
| 2007/0265680 | A1 | 11/2007 | Liu |
| 2009/0210026 | A1 | 8/2009 | Solberg |
| 2009/0292341 | A1 | 11/2009 | Parramon |
| 2010/0069992 | A1 | 3/2010 | Aghassian |
| 2010/0211132 | A1 | 8/2010 | Nimmagadda |
| 2010/0324624 | A1 | 12/2010 | Chang |
| 2010/0327887 | A1 | 12/2010 | Denison |
| 2011/0106220 | A1 | 5/2011 | DeGiorgio |
| 2011/0112603 | A1 | 5/2011 | DeGiorgio |
| 2011/0172739 | A1 | 7/2011 | Mann |
| 2011/0218589 | A1 | 9/2011 | DeGiorgio |
| 2011/0218590 | A1 | 9/2011 | DeGiorgio |
| 2012/0022612 | A1 | 1/2012 | Littlewood |
| 2012/0259390 | A1 | 10/2012 | Canion |
| 2013/0041396 | A1 | 2/2013 | Ryotokuji |

OTHER PUBLICATIONS

"Electroacupuncture." http://en.wikipedia.org/wiki/Electroacupuncture.

Cheung. The Mechanism of Acupuncture Therapy and Clinical Case Studies. Taylor and Francis, published in London. 2001. ISBN 0-415-27254-8. The Forward, Chapters 1-3, and 5.

Li. "Neural Mechanism of Electroacupuncture's Hypotensive Effects", Autonomic Neuroscience: Basic and Clinical 157 (2010) 24-30.

"Acupuncture Today: Electroacupuncture". Feb. 1, 2004. (Retrieved on-line Aug. 9, 2006 at http://www.acupuncturetoday.com/abc/electroacupuncture.php.).

"Acupuncture." http://en.wikipedia.org/wiki/Acupuncture.

Peterson, U.S. Appl. No. 61/674,691, filed Jul. 23, 2012.

Thenuwara, U.S. Appl. No. 61/676,275, filed Jul. 26, 2012.

Peterson, U.S. Appl. No. 61/606,995, filed Mar. 6, 2012.

Greiner, U.S. Appl. No. 13/598,582, filed Aug. 29, 2012.

Greiner, U.S. Appl. No. 61/575,869, filed Aug. 30, 2011.

Peterson, U.S. Appl. No. 61/609,875, filed Mar. 12, 2012.

Peterson, U.S. Appl. No. 61/672,257, filed Jul. 16, 2012.

Peterson, U.S. Appl. No. 61/672,661, filed Jul. 17, 2012.

Peterson, U.S. Appl. No. 61/673,254, filed Jul. 19, 2012.

Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.

Greiner, U.S. Appl. No. 13/622,653, filed Sep. 19, 2012.

Greiner, U.S. Appl. No. 13/630,522, filed Sep. 28, 2012.

Greiner, U.S. Appl. No. 13/630,322, filed Sep. 28, 2012

Greiner, U.S. Appl. No. 13/622,497, filed Sep. 19, 2012.

* cited by examiner

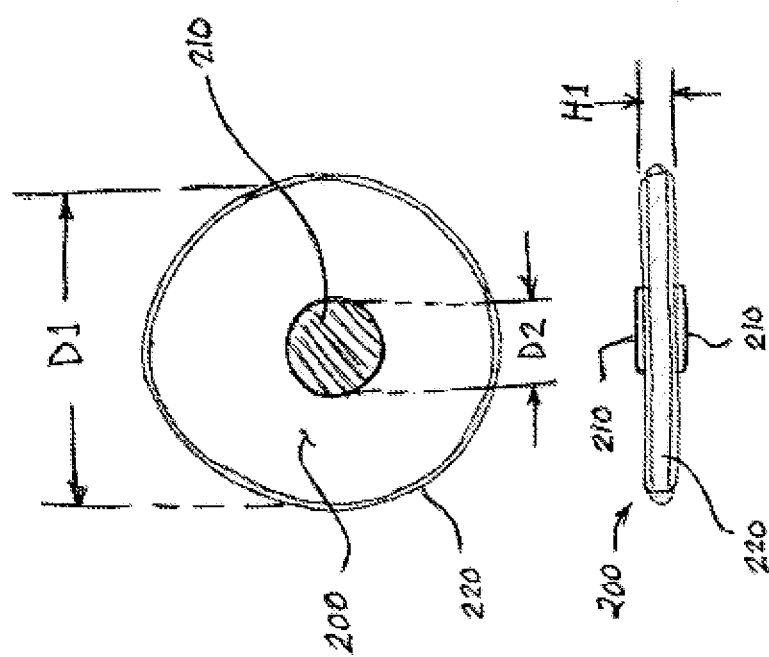

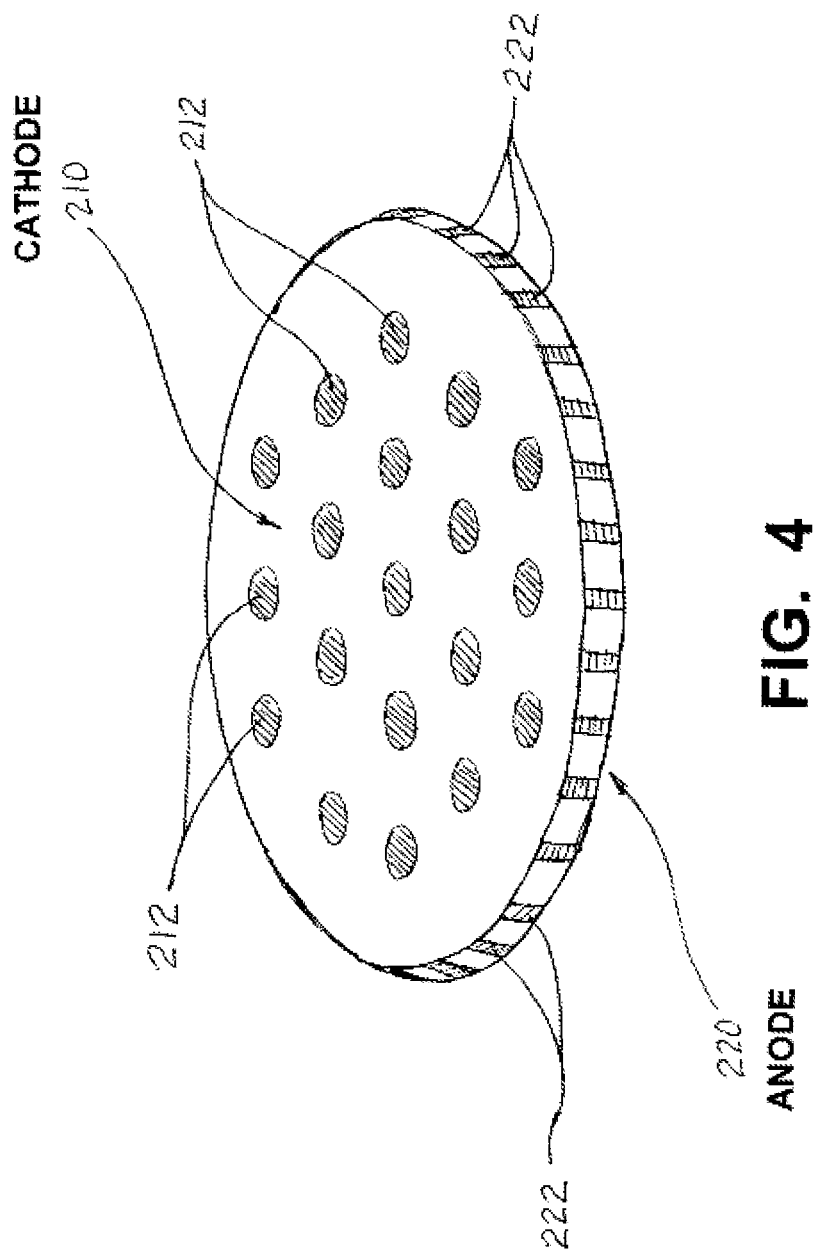

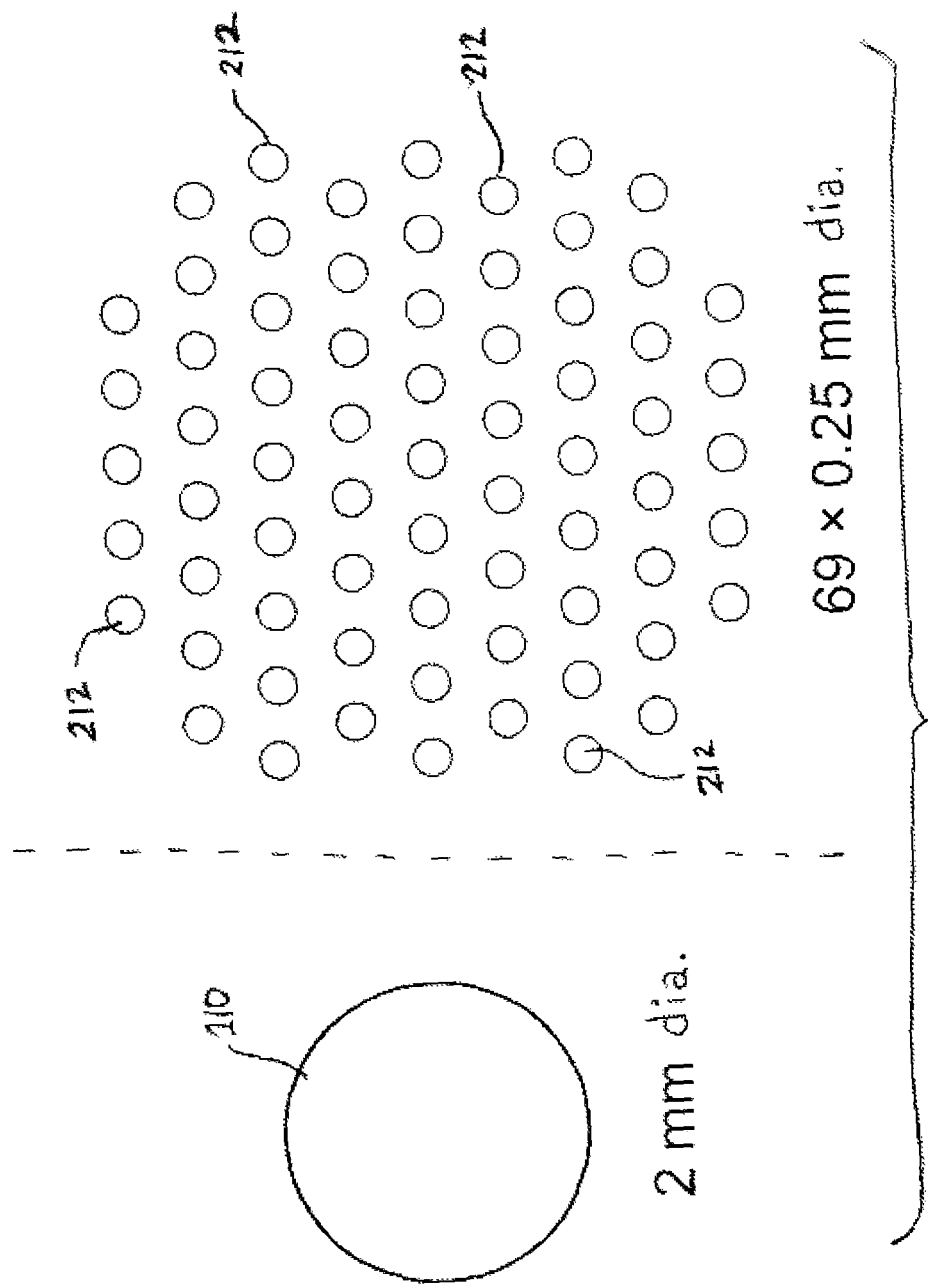

TABLE 1
A comparison of electrode diameters (D) and numbers of electrodes (N) for 316 Stainless Steel (SS) and Platinum (Pt)

| D (mm) | A (mm²) | N | PW (ms) | I (mA) | Q (uC) | uC/mm² | SS (0.3-0.4 uC/mm²) | Pt (2-3 uC/mm²) |
|---|---|---|---|---|---|---|---|---|
| 2 | 3.142 | 1 | 0.5 | 4 | 2 | 0.637 | Red | Green |
| 2 | 3.142 | 2 | 0.5 | 4 | 2 | 0.318 | Yellow | Green |
| 0.25 | 0.049 | 68 | 0.5 | 4 | 2 | 0.599 | Red | Green |
| 0.25 | 0.049 | 136 | 0.5 | 4 | 2 | 0.300 | Green | Green |
| 3 | 7.069 | 1 | 0.5 | 4 | 2 | .283 | Green | Green |
| 2 | 3.142 | 1 | 0.5 | 25 | 12.5 | 3.979 | Red | Red |
| 2 | 3.142 | 2 | 0.5 | 25 | 12.5 | 1.989 | Red | Green |
| 3 | 7.069 | 1 | 0.5 | 25 | 12.5 | 1.768 | Red | Green |
| 3 | 7.069 | 1 | 0.5 | 25 | 12.5 | 1.768 | Red | Green |
| 4 | 12.566 | 1 | 0.5 | 25 | 12.5 | 0.995 | Red | Green |
| 4 | 12.566 | 2 | 0.5 | 25 | 12.5 | 0.497 | Red | Green |
| 0.25 | 0.049 | 68 | 0.5 | 25 | 12.5 | 3.745 | Red | Red |
| 0.25 | 0.049 | 136 | 0.5 | 25 | 12.5 | 1.872 | Red | Green |
| 4 | 12.566 | 1 | 0.5 | 10 | 5 | 0.398 | Yellow | Green |
| 4 | 12.566 | 1 | 0.5 | 7.5 | 3.75 | 0.298 | Green | Green |

FIG. 5A

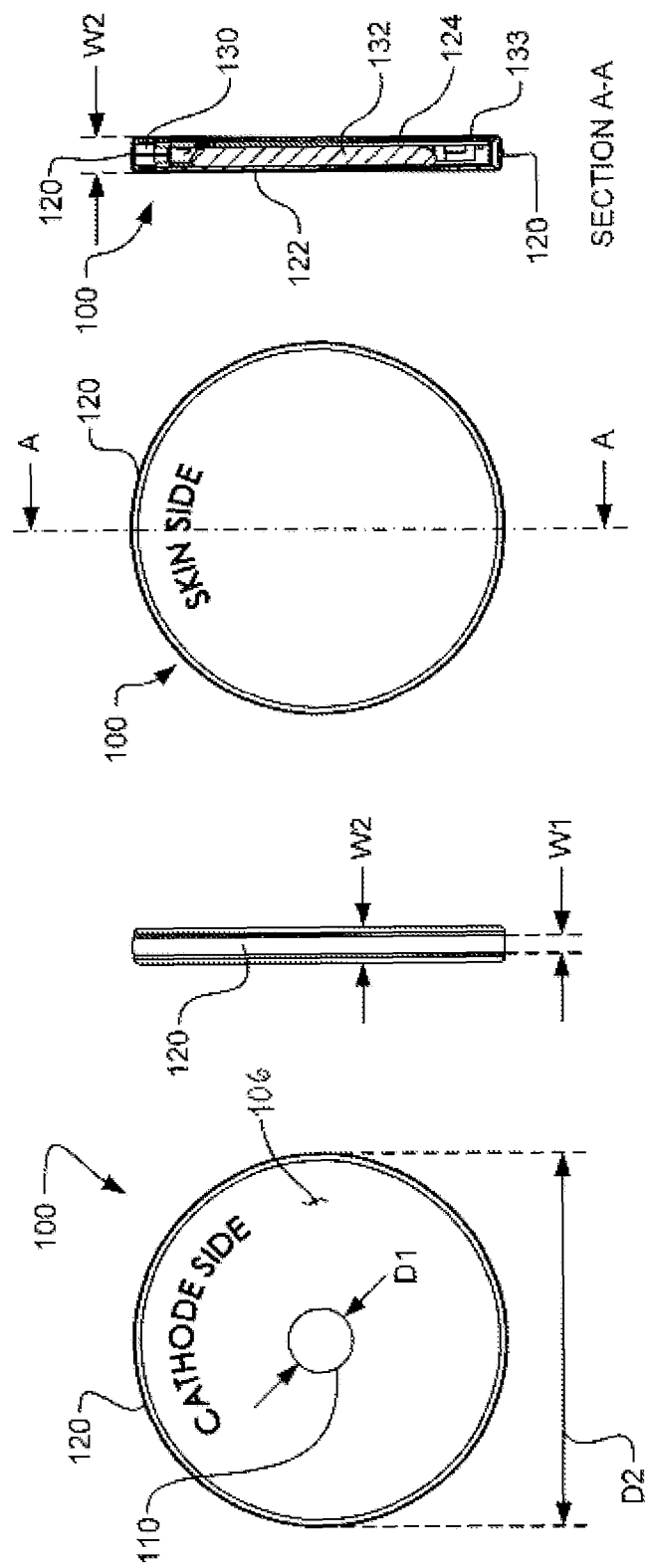

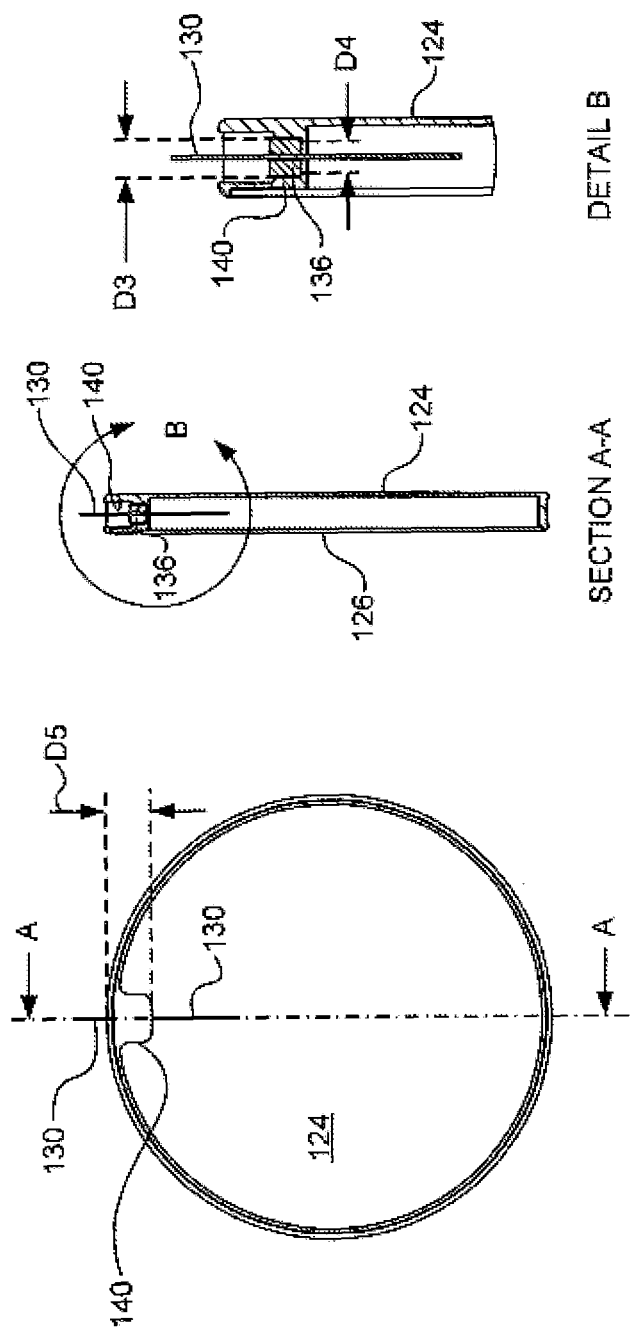

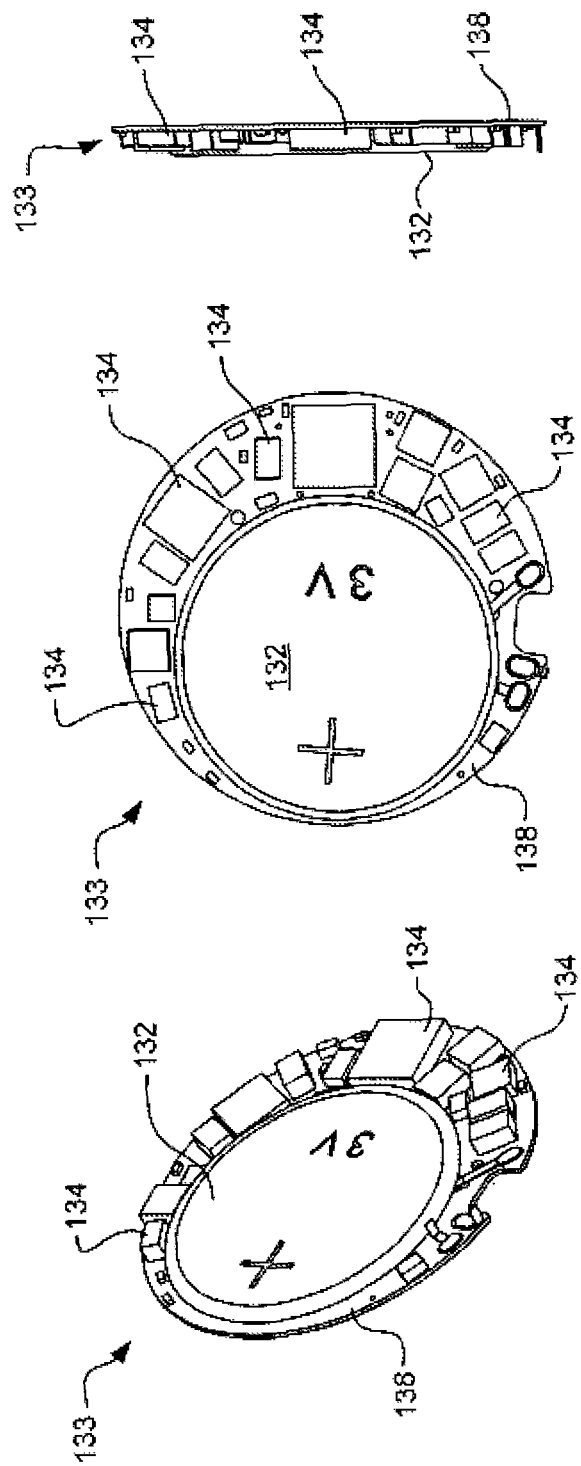

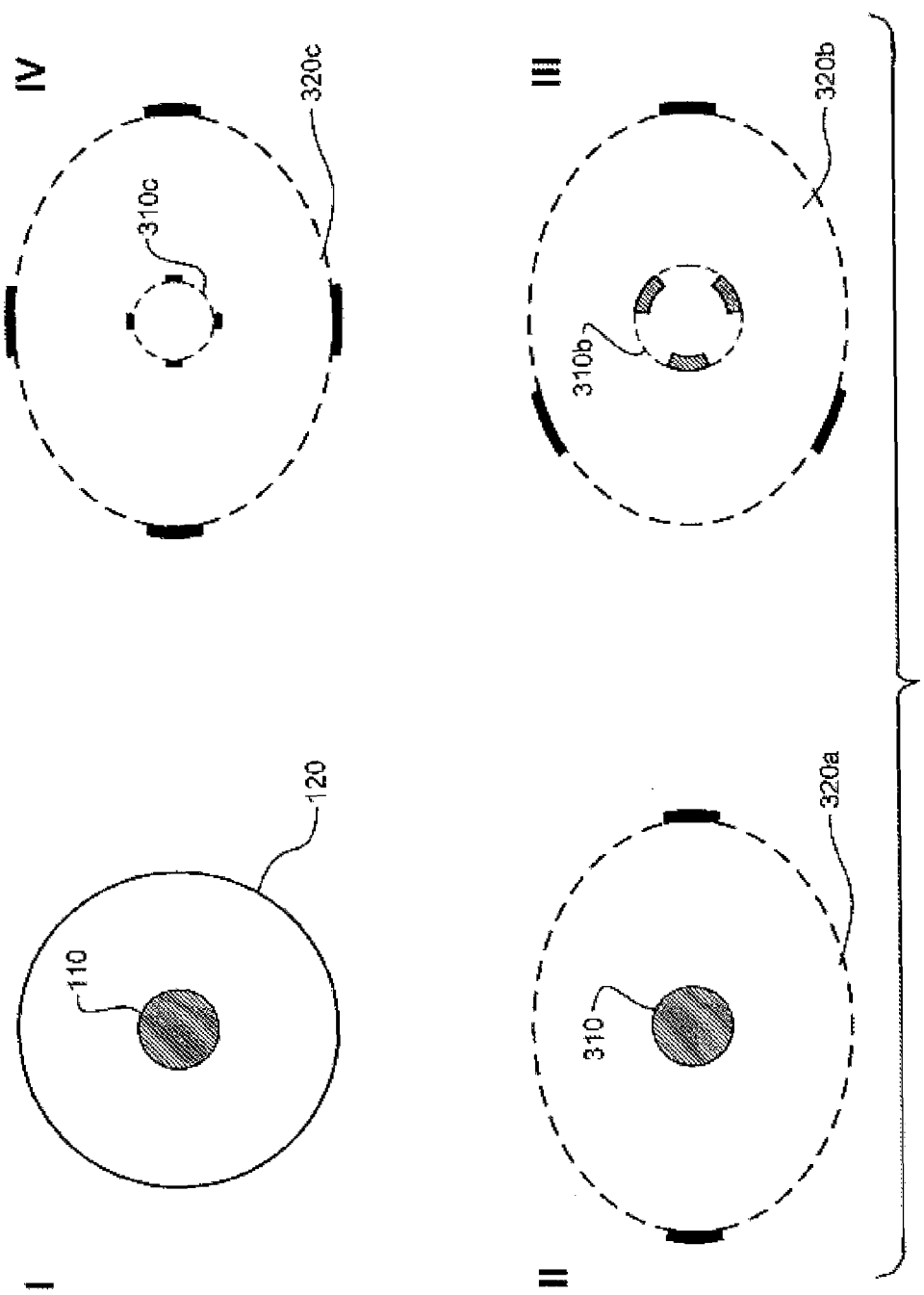

ELECTRODE CONFIGURATION FOR AN IMPLANTABLE ELECTROACUPUNCTURE DEVICE

RELATED APPLICATIONS

This application is a Continuation-In-Part (CIP) of U.S. patent application Ser. No. 13/598,582, filed Aug. 29, 2012, which application is incorporated herein by reference in its entirety, including all drawings and appendices. This application also claims the benefit of the following previously-filed U.S. Provisional Patent Applications, which applications are also incorporated hereby by reference:

1. Application No. 61/606,995, filed Mar. 6, 2012, entitled "Electrode Configuration For Implantable Electroacupuncture Device"; and
2. Application, No. 61/676,275, filed Jul. 26, 2012, entitled "Radial Feed-Through Packaging for an Implantable Electroacupuncture Device".

BACKGROUND

The present disclosure describes improvements to the electrodes employed when using and operating a small, thin coin-sized electroacupuncture (EA) device of the type described in the related applications referenced above in Paragraph [0001], or equivalent small, self-contained, stimulators adapted for implantation under the skin. More particularly, the present disclosure relates to a preferred scheme for configuring the electrodes on the housing of an implantable EA device.

In accordance with the teachings of the applications referenced above, a self-contained, coin-sized stimulator may be implanted in a patient at or near a specified target tissue location, e.g., one or more acupoint(s), in order to favorably treat a condition or disease of a patient. The coin-sized stimulator referenced in the previously-filed patent applications is referred to as an implantable electroacupunture device (IEAD). Such IEAD advantageously applies electrical stimulation pulses at very low duty cycles in accordance with a specified stimulation regimen through electrodes that either form an integral part of the housing of the stimulator, or are closely coupled thereto through a very short lead. A small, thin, coin-cell type battery inside of the IEAD case provides enough stored energy for the IEAD to carry out its specified stimulation regimen over a period of several years. Thus, the IEAD, once implanted, provides an unobtrusive, needleless, long-lasting, elegant and effective mechanism for treating certain conditions and diseases that have long been treated by acupuncture or electroacupuncture.

The ability of the IEAD to apply its low level stimulation through the electrodes that are attached to, carried by, or otherwise form a part of the housing of the IEAD is, in large part, a function of how well such electrodes are able to direct and focus the applied stimulation to the target tissue location(s) of interest, e.g., a designated acupoint(s), and to the tissue and nerves associated with such target location. The present disclosure is directed to techniques and schemes that accomplish that goal.

It is noted that traditional acupuncture and acupressure have been practiced in Eastern civilizations (principally in China, but also in other Asian countries) for at least 2500 years. It is still practiced today throughout many parts of the world, including the United States and Europe.

Acupuncture is an alternative medicine that treats patients by insertion and manipulation of needles in the body at selected points. The locations where the acupuncture needles are inserted are referred to as "acupuncture points" or simply just "acupoints". The location of acupoints in the human body has been developed over thousands of years of acupuncture practice, and maps showing the location of acupoints in the human body are readily available in acupuncture books or online, see, e.g., *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). This reference, i.e., the *WHO Standard Acupuncture Point Locations* 2008, is incorporated herein by reference.

In classical acupuncture treatment, once needles are inserted at a desired acupoint location(s), the needles are typically mechanically modulated for a short treatment time, e.g., 30 minutes or less. The needles are then removed until the patient's next visit to the acupuncturist, e.g., in 1-4 weeks (or longer), when the process is repeated. Over several visits, the patient's condition or disease is effectively treated, offering the patient needed relief and improved health.

In electroacupuncture (EA) treatment, needles are inserted at specified acupoints, as in classical acupuncture treatment, but the needles, once inserted, are then connected to an external source of electrical radio frequency (RF) energy, and electrical stimulation signals, at a specified frequency and intensity level, are then applied to the patient's body through the needles at the acupoint(s), thereby also providing the patient with a measure of needed and desired treatment for his or her condition or disease.

While some controversy may still exist as to the precise mechanism by which the insertion of needles into body tissue at selected acupoint(s) achieves its beneficial results, the successful activation of nerve fibers (whether through mechanical modulation or electrical modulation) at the acupoint(s) is thought by most to be a key element necessary for effective acupuncture treatment. See, e.g., "Longhurst, Defining Meridians: A Modern Basis of Understanding," *J Acupunct Meridian Stud* 2010; 3(2):67-74

U.S. Pat. No. 6,735,475, issued to Whitehurst et al., discloses use of an implantable miniature neurostimulator, referred to as a "microstimulator," that can be implanted into a desired tissue location and used as a therapy for headache and/or facial pain. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize (i) large implantable stimulators having long leads that must be tunneled through tissue or blood vessels over an extended distance to reach the desired stimulation site, (ii) external devices that must interface with implanted electrodes via percutaneous leads or wires passing through the skin, or (iii) inefficient and power-consuming wireless transmission schemes. Such devices and methods are far too invasive, and/or are ineffective the treatment provided.

From the above, it is seen that there is a need in the art for a less invasive device and technique for electroacupuncture stimulation of acupoints, or other target tissue locations, that does not require the continual use of needles inserted through the skin, or long insulated wires implanted or inserted into blood vessels, for the purpose of treating an illness or deficiency of a patient.

Moreover, as will be seen from the description that follows, the electrodes used with any implantable electroacupuncture device must be optimally configured so that the applied stimulation current achieves its intended purpose of acting and interacting with nerve fibers and tissue so as to produce desired efficacious results. The innovations described herein address that need.

SUMMARY

An implantable electroacupuncture device (IEAD) is described herein that includes a coin-sized and -shaped housing having a top surface, a bottom surface and a perimeter edge connecting the top surface to the bottom surface. A preferred construction has electrodes configured so as to reside on, or form an integral part of, the surfaces of the housing. One preferred electrode configuration has electrodes on the top and/or bottom surfaces functioning as cathodes, and an electrode on the perimeter edge of the housing functioning as an anode. The cathodic electrodes may, in some configurations, be divided into segments, or an array of smaller cathodic electrodes, each of which, or groups of which, may be selectively turned ON or OFF so as to provide a convenient mechanism for adjusting the density of the stimulus current flowing through the cathodic electrode surface area. The anodic electrode, which in its simplest form is a ring electrode on the perimeter edge surface, may likewise in some configurations be divided into segments or an array of smaller anodic electrodes spaced around the perimeter edge. By selectively controlling the current density and spacing between the anodic and cathodic electrodes, an optimum stimulus current may be generated that minimizes electrode corrosion and current shunting, yet achieves a desired range or depth penetration of the stimulus current into the body tissue that surrounds the EA device when the EA device is implanted in a patient's body.

One configuration of the implantable EA device disclosed herein may be characterized as an EA device adapted to be implanted at a specified tissue location, e.g., at a specific acupoint of a patient. The EA device includes (i) a housing; (ii) at least one cathodic electrode and at least one anodic electrode formed on, or as an integral part of, the housing; and (iii) stimulation circuitry residing inside the housing and electrically coupled to the at least one cathodic and at least one anodic electrodes. The stimulation circuitry is configured, i.e., designed or programmed, to generate stimulation pulses that are delivered to body tissue through the at least one cathodic and at least one anodic electrodes in accordance with a prescribed stimulation regimen. In a preferred configuration, the at least one cathodic electrode resides on a top and/or bottom surface of the housing and utilizes an optimum surface area for activation, where "activation" as used herein relates to electrically connecting the electrode (or a prescribed portion of the electrode surface area) to the stimulation circuitry so that the electrode is turned ON (as opposed to being turned OFF, when the electrode is not electrically connected to the stimulation circuitry). An "optimum surface area" for activation comprises an electrode surface area that allows a desired current density to flow through the electrode surface area without causing electrode corrosion or current shunting to occur. Electrode corrosion and current shunting are discussed in more detail in the Detailed Description, below.

Another configuration of the invention disclosed herein may be characterized as an IEAD adapted to be implanted at a specified acupoint of a patient. The IEAD is coin-sized and -shaped, having a top surface, a bottom surface, and a perimeter edge connecting the top surface to the bottom surface. At least one cathodic electrode and at least one anodic electrode are formed on, or comprise an integral part of, the surfaces of the IEAD housing. Typically, the at least one cathodic electrode is on the top or bottom surface of the housing, and the at least one anodic electrode is on the perimeter edge surface of the housing. Stimulation circuitry resides inside the housing and connection means are employed that electrically couple the at least one cathodic electrode and the at least one anodic electrode to the stimulation circuitry. The stimulation circuitry generates charge balanced monophasic stimulation pulses of electrical current that are delivered to body tissue surrounding the housing through the at least one cathodic electrode and the at least one anodic electrode in accordance with a prescribed stimulation regimen. The at least one cathodic electrode has a surface area sufficiently large to allow a desired current density to flow through it without causing electrode corrosion. Further, the at least one cathodic electrode is positioned sufficiently far from the at least one anodic electrode so as to prevent current shunting to occur between the at least one cathodic electrode and the at least one anodic electrode before the stimulation pulses of electrical current have penetrated into the body tissue a desired distance.

Still another configuration of the invention disclosed herein may be characterized as a method of operating an IEAD. The IEAD with which the method is used includes a housing having at least two electrodes carried on, or formed as an integral part of, the housing. Stimulation circuitry resides within the housing and is coupled to the at least two electrodes. The stimulation circuitry generates stimulation pulses of a prescribed frequency, intensity and pulse width. These stimulation pulses are applied to the at least two electrodes in accordance with a prescribed stimulation regimen. The method of operating the EA device includes: (i) configuring one of the at least two electrodes to be a cathodic electrode, and placing the cathodic electrode on a top and/or bottom portion of the housing; (ii) configuring the other of the at least two electrodes to be an anodic electrode, and placing the anodic electrode on a perimeter edge of the housing; and (iii) applying monophasic electrical stimulation to the anodic and cathodic electrodes during a stimulation session that lasts T3 minutes at a rate of once every T4 minutes, during which stimulation session monophasic stimulation pulses having a pulse width of T1 milliseconds (msec) are applied through the cathodic and anodic electrodes at a rate of once every T2 msec. In accordance with this method, the value of T1 is between 0.1 and 0.6 msec, T2 is between 200 and 1000 msec, T3 is between 10 and 60 minutes, and the ratio of T3/T4 is no greater than 0.05.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 3 shows a top (or bottom) view of the cathode and anode electrodes used with the coin-sized stimulator of FIG. 2.

FIG. 3A shows a side view of the cathode and anode electrodes used with the stimulator of FIG. 3.

FIG. 4 shows a second embodiment of an optimized electrode pair placed on a coin-sized stimulator housing.

FIG. 5 illustrates two ways of achieving a desired electrode contact surface area with either a single electrode surface area, shown on the left, or with an array of multiple smaller electrode surface areas, shown on the right.

FIG. 5A shows a table that compares some electrode diameters and numbers of electrodes for 316SS (SS) and Platinum (Pt) for a current stimulus pulse having a pulse width of 0.5 milliseconds at various amplitudes expressed in milliamps.

FIG. 12 shows a plan view of one surface (identified in FIG. 12 as the "Cathode Side") of the IEAD housing illustrated in FIG. 9.

FIG. 12A shows a side view of the IEAD housing illustrated in FIG. 9.

FIG. 13 shows a plan view of the other side, indicated as the "Skin Side," of the IEAD housing or case illustrated in FIG. 9.

FIG. 13A is a sectional view of the IEAD of FIG. 3 taken along the line A-A of FIG. 13.

FIG. 15 is a plan view of the empty IEAD housing shown in FIG. 14.

FIG. 15A depicts a sectional view of the IEAD housing of FIG. 15 taken along the section line A-A of FIG. 15.

FIG. 15B shows an enlarged view or detail of the portion of FIG. 15A that is encircled with the line B.

FIG. 16 is a perspective view of an electronic assembly, including a battery, adapted to fit inside of the empty housing of FIG. 14 and FIG. 15.

FIGS. 16A and 16B show a plan view and side view, respectively, of the electronic assembly shown in FIG. 16.

FIG. 17A schematically illustrates a few alternative electrode configurations that may be used with the IEAD of FIG. 9.

Figure 1:
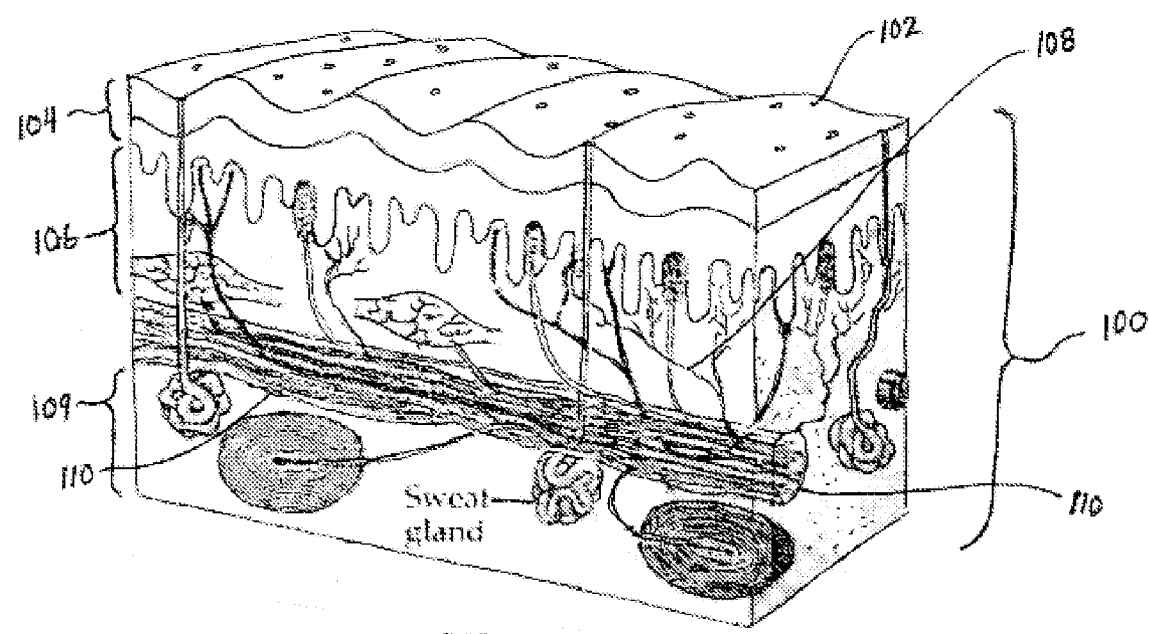
FIG. 1 is a three-dimensional sketch of human skin tissue, including the subcutaneous tissue area below the outer layer of the skin.

Appendix A, submitted herewith, illustrates some examples of alternate symmetrical electrode configurations that may be used with an IEAD of the type described herein.

Appendix B, submitted herewith, illustrates a few examples of non-symmetrical electrode configurations that may be used with an IEAD made in accordance with the teachings herein.

Appendix C, submitted herewith, shows an example of the code used in the micro-controller IC (e.g., U2 in FIG. 21) to control the basic operation and programming of the IEAD, e.g., to turn the IEAD ON/OFF, adjust the amplitude of the stimulus pulse, and the like, using only an external magnet as an external communication element.

Appendices A, B and C are incorporated by reference herein.

Throughout the drawings, identical reference numbers designate similar, but not necessarily identical, elements.

DETAILED DESCRIPTION

Overview

Disclosed and claimed herein are preferred electrode configurations for use with a coin-sized and -shaped subcutaneously implantable electroacupuncture device (IEAD). The preferred electrode configuration(s) is placed on, or incorporated within, the housing of the IEAD. The IEAD is adapted to be implanted subcutaneously through a very small incision, e.g., less than 2-3 cm in length, directly adjacent to, or at, a selected acupuncture site (or other target nerve/tissue location). In accordance with the teachings herein, the IEAD is subcutaneously implanted so that its electrodes are located and anchored at a desired target tissue stimulation site, which target site may also be referred to as an acupuncture site, or "acupoint." The acupoint is selected based on its known history of moderating or positively affecting a physiological or health condition of a patient that needs treatment. Stimulation pulses are applied by the EA device at the selected acupoint at a very low duty cycle in accordance with a specified stimulation regimen. This stimulation regimen is designed to provide effective electroacupuncture (EA) or electrostimulator (ES) treatment for a patient.

The Parent Application referenced above in Paragraph [0001] provides a description of an IEAD, system and/or method used to treat a particular disease or condition of a patient, e.g., hypertension. The present application describes in more detail a preferred configuration or manner of constructing or forming or orienting electrodes adapted to be used with such an IEAD. Such electrodes are sometimes referred to in the Parent Application, for some embodiments therein disclosed, as "needle electrodes". However, as the description below indicates, the electrodes are not necessarily needle-shaped, but rather typically comprise relatively smooth surfaces that reside on or near the housing of the IEAD at various locations and orientations.

It is a feature of the electrodes disclosed herein that when subcutaneously placed so as to reside at or near a desired acupoint, or other target tissue location, and when electrically energized so as to cause a small electrical field to emanate from the electrodes, such electrical field causes a small electrical current to flow in the body tissue surrounding the acupoint. For an optimally designed electrode, this electrical current, in turn, activates as many targeted nerve fibers as possible. Such nerve fiber activation is then able to achieve the greatest therapeutic effect. In order to optimally achieve such desired nerve fiber activation, with the least expenditure of energy and fewest clinical side effects, the directionality of the nerve fibers and proximity to the electrode is a factor that must be considered in the electrode design.

The directionality of the nerve fibers is illustrated in FIG. 1, which shows a three-dimensional sketch of skin tissue 100 of a human body. The skin tissue 100 illustrated in FIG. 1 includes the outer layer of the skin, or epidermis 104, and the dermis 106. The top surface 102 of the epidermis 104 comprises the skin layer that is visible and exposed to the environment around the human body. Much of the epidermis comprises dead cells impregnated with keratin. The dermis 106 is the thick layer of living tissue that lies beneath the epidermis. The dermis consists mainly of loose connective tissue within which are blood capillaries, lymph vessels, sensory nerve endings, sweat glands and their ducts, hair follicles, sebaceous glands, and smooth muscle fibers. For purposes of the present disclosure, the term "subcutaneously" refers broadly to anything "beneath the skin", which in the context of this disclosure most often means below the dermis 106. Hence, subcutaneous tissue is loose connective tissue, often fatty, situated under the dermis 106.

Still referring to FIG. 1, it is seen that groups of individual nerve fibers 108 often congregate together to form a bundle of nerve fibers 110. This bundle of nerve fibers 110 is located beneath the dermis 106, and generally runs parallel to the surface 102 of the skin. Some individual nerve fibers 108, near their respective distal ends, extend away from the bundle 110 in a direction towards the skin surface, or to some other destination. These nerves, at or near their respective distal ends, thus generally run orthogonal to the surface of the skin.

Thus, as illustrated in FIG. 1, the directionality of the nerve fiber bundles 110 is parallel to the surface 102 of the skin, while the directionality of individual nerve fibers 108 is also predominantly parallel to the surface of the skin, with relatively short portions of some individual nerve fibers being generally orthogonal to the surface of the skin 102.

Cathodic stimulation preferentially activates nerve fibers running tangential or parallel to the face of the electrode. This is in contrast to anodic stimulation which preferentially activates nerve fibers that run radial or perpendicular to the face of the electrode surface. As indicated above, individual nerve fibers 108 that go to or near the skin surface 102 generally run parallel and above the subcutaneous space 109 before curving upwards into the dermis 106. Similarly, nerve fibers 108 in the subcutaneous space 109 run parallel to this space 109 before curving deeper into deeper layers of tissue.

Hence, as a first aspect of electrode design for a subcutaneously-placed implanted device, such as a small coin-sized IEAD described herein, it is seen that the cathodic and anodic electrode surfaces need to be optimally configured and placed. These electrode surfaces, for the coin-sized implantable devices, are preferably formed on, or as an integral part of, the housing of the device. Where cathodic stimulation is used, which is common for most implantable tissue-stimulation devices, and where the configuration of the electrode is to be optimized to activate as many nerves as possible at or near a specified acupoint, it is beneficial to have a cathode electrode positioned closest to the cutaneous layers above the device as well as to tissue layers below the device. Any curvature of the nerves away from these cathode-covered surfaces further reduces the threshold current needed to activate them electrically. Exposure to anodes should thus be limited to the edges of the device where nerve fibers are oriented predominantly perpendicular to the electrode surface.

A second aspect for the electrode design is the proximity of the nerve fiber relative to the size of the electrode. It is noteworthy that activation in both the case of a cathode or an anode depends upon the magnitude of the second spatial derivative of the applied electric field potential along the axis of the nerve fiber. A uniform electric field from a continuous flat plate electrode, for example, results in a second spatial derivative of voltage which is zero in all directions and theoretically would not activate nerve fibers regardless of the applied current. The ideal electrode in this respect would thus be a point source since this maximizes the second spatial derivative of the field potential as the nerve fiber approaches the electrode surface.

Mathematically this can be seen relatively easily for a spherical electrode contact of radius R in a uniform volume conductor with conductivity $\rho$. The field potential V, for a current I at the surface of the electrode is $$V = \frac{\rho I}{4\pi} \times \frac{1}{R}. \quad (1)$$

The second spatial derivative of voltage perpendicular to the surface is $$\frac{d^2 V}{d r^2} = \frac{\rho I}{4\pi} \times \frac{1}{R^3}. \quad (2)$$

Equation (2) is the activating function for a nerve aligned radial or perpendicular to the surface of the electrode (defined as the r direction). There is clearly a much greater activating function magnitude for nerve fibers near the surface of the electrode with a smaller radius electrode. The second spatial derivative of voltage tangential to the surface is $$\frac{d^2 V}{d x^2} = \frac{\rho I}{4\pi} \times \left(-\frac{1}{R^3}\right). \quad (3)$$

Equation (3) is the activating function for a nerve aligned tangential or parallel to the surface of the electrode (defined as the x direction). The sign is negative meaning that the activating function is positive for a cathodic or negative current I. This reflects how nerves running parallel to the electrode are optimally depolarized by cathodic stimulation. Again, there is clearly a much greater activating function magnitude for nerve fibers at the surface with a smaller radius electrode.

Theoretically, smaller electrode contacts are always more efficient at electrically activating tissue. This applies even to non-spherical electrode contacts. In practice, however, the minimum size of the electrode is limited by maximum current density that can be safely injected and the available compliance voltage of the stimulator to drive current through the smaller, and thus higher impedance, electrode.

Figure 2:
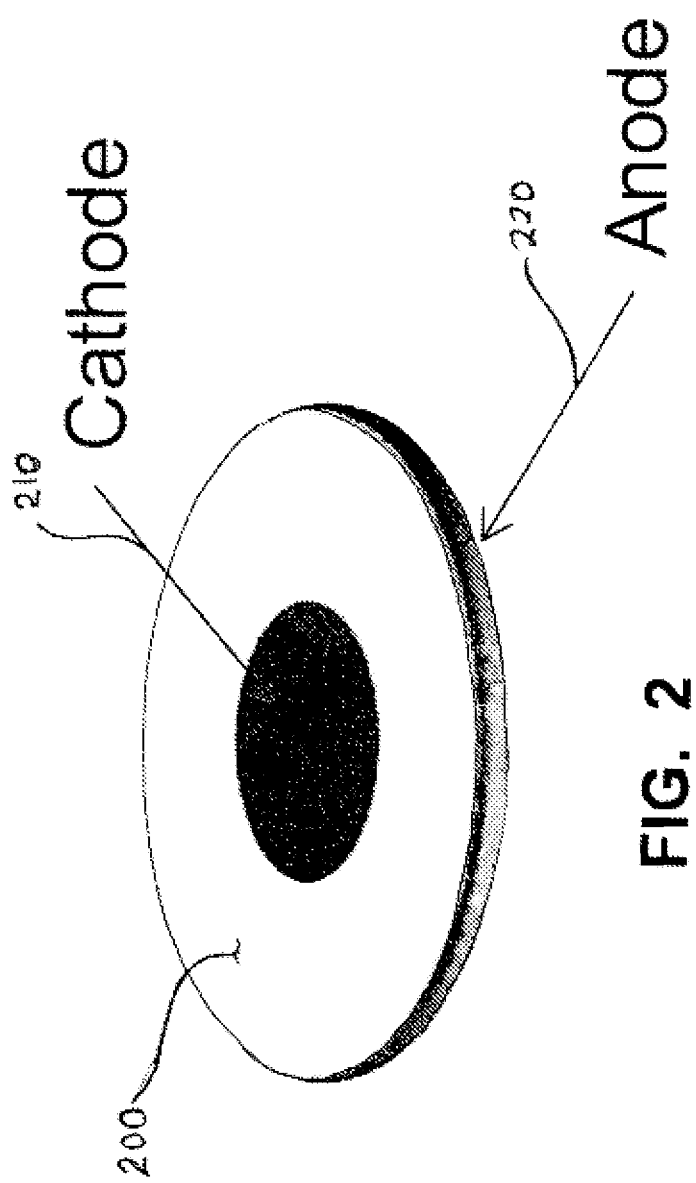
FIG. 2 shows a first embodiment of a representative optimized electrode pair, both cathode and anode, placed on a coin-sized stimulator housing.

Turning back then to the optimal electrode configuration for an electrical stimulation device placed at an acupuncture point (or acupoint), it is seen that the optimal electrode configuration takes on a form wherein: (i) small cathodes are distributed on the upper and lower surfaces of the device parallel to the skin and (ii) small anodes are distributed on the edges of the device which are perpendicular to the skin. This optimal electrode configuration is shown in FIG. 2, where a Cathode electrode 210 is formed on the top and/or bottom surfaces of a coin-sized device housing 200 (note, the bottom of the housing is not visible in FIG. 2), while an Anode electrode 220 is formed as a thin ring electrode around the edge or perimeter of the housing 200.

Current shunting may occur if the distance between the anode and cathode is too close. Current shunting applies to surface area only in that a larger surface area of a cathode necessarily brings the edges of the cathode closer to the anode ring. Thus, in optimizing the electrode configuration, the size of the electrode must be considered to prevent damage to the electrode material when the desired current density is used (which tends to happen if the electrode area is too small) and to prevent current shunting when the edges of the cathode get too close to the anode ring (which tends to happen when the electrode area is too large.

A further aspect of the electrode configuration design is how to optimally space electrode contacts on the surface of the housing 200 of such a device. In the simple embodiment depicted in FIGS. 2, 3 and 3A, there are single small cathodes 210 centered on the top and bottom of the device housing 200 with a thin ring anode 220 around the edge of the device 200. The surface area of these electrode contacts would be the minimum for safe stimulation without electrode corrosion and/or tissue damage. For an electrode material such as 316 LVM stainless steel, for example, up to 0.3-0.4 microCoulombs/mm$^2$ might be safely injected during a stimulus pulse. (Note: a Coulomb is the basic measure of electrical charge, and electrical current, measured in Amperes (A), is defined as the rate at which electrical charge flows, or Coulombs per Second.)

As further depicted in FIGS. 3 and 3A, the housing 200 is disc-shaped (also referred to herein as "coin-shaped"), having a diameter D1. The cathodic electrodes 210, located on the top and bottom surfaces of the disc-shaped housing 200, have a diameter D2. The housing 200 has a thickness of H1. Thus, the anodic electrode 220 is essentially a ring-shaped electrode having a width of about H1, or a little less than H1, e.g., 0.2-0.4 mm less than H1, and a diameter of D1. In one configuration, the diameter D1 of the disc-shaped housing may be approximately 22 mm, whereas the diameter of the cathodic electrode surface area D1 may range from 2-10 mm. The height H1, or thickness, of the disc-shaped housing 200 typically is in the range of 1.4-2.5 mm.

Should the device housing 200 have a surface area larger than the minimum safe electrode contact area and the cathode to anode spacing is sufficient to avoid current shunting, then a good electrode configuration to use would be to distribute the same electrode surface area over multiple contacts, as depicted in FIG. 4. As seen in FIG. 4, the cathode electrode 210 comprises multiple smaller cathodic electrode contacts 212 distributed over the top and/or bottom surface of the housing 200. (Note, again, the bottom surface of the housing 200 is not visible in FIG. 4, but it looks substantially identical as the top surface, which is visible in FIG. 4.) Similarly, the anodic electrode 220 comprises multiple smaller anodic electrode contacts 222 distributed around the peripheral edge of the housing 200.

The electrode configuration shown in FIG. 4 advantageously distributes the electrode activating function over more of the surface area of the device housing 200 while preserving the ability to use the highest current density and thus highest activating function possible at each electrode contact.

A typical center-to-center spacing for like polarity contacts should preferably be less than twice the individual contact diameter in order to minimize gaps in the activation function. Opposite polarity contacts should preferably be spaced at least twice the individual contact diameter to minimize current shunting. The individual contact diameter and spacing may be chosen as needed to distribute the electrode contacts over as much of the surface area as possible at the highest available current density.

By way of example, if an IEAD is designed to deliver a sequence of electrical pulses having a duration of 0.5 milliseconds (msec) at an amplitude up to 4 milliamps (mA) (i.e. the pulse charge delivered with each pulse is 0.5 msec×4 mA=2 microcoulombs), then an electrode contact surface area of 2 microcoulombs÷0.3 microcoulombs/mm$^2$=6.7 mm$^2$ would be required when using 316 LVM stainless steel as the electrode material. Such electrode surface area could be realized using two disk cathode contacts with a 2 mm diameter on the upper and lower surface, as illustrated on the left side of FIG. 5. Alternatively, each cathode contact could be spread out over approximately 68 contacts with a 0.25 mm diameter spaced out at 0.5 mm center to center, as shown on right side of FIG. 5. Either electrode configuration achieves the same total surface area, but the configuration having approximately 68 contacts (shown on the right side of FIG. 5) increases the area over which the activating function can be applied for nerves close to the electrode by a factor of roughly 4.

It should be noted that 316 LVM stainless steel (sometimes referred to herein as just "316SS" or "316 stainless steel") may not be the ideal electrode material if higher current amplitudes are desired or needed. Stainless steel 316SS has a limited charge injection capacity of about 0.3 to 0.4 $\mu C/mm^2$. In contrast, platinum has a charge injection capacity of 2 to 3 $\mu C/mm^2$, almost 10 times as great as 316SS. Hence, where large current amplitudes are needed, the best electrode material would platinum.

FIG. 5A shows a table, TABLE 1, that compares some electrode diameters (D) and numbers of electrodes (N) for 316SS (SS) and Platinum (Pt), for a current stimulus pulse having a pulse width (PW) of 0.5 millisecond (ms) at various amplitudes (I), expressed in milliamps (mA). Included in the table is the pulse charge (Q) delivered with each pulse, expressed in microcoulombs ($\mu C$). Also included in TABLE 1 (FIG. 5A) is a color code that indicates whether the indicated electrode size can support the charge injection that would be required for the indicated surface area of the electrode, current amplitude and pulse width. A "Green" color code indicates the charge can be injected safely. A "Yellow" code indicates a marginal condition, and a "Red" code indicates a charge level above the accepted limit. Thus, as can be seen from TABLE 1, with a single 4 mm diameter stainless steel electrode, the maximum current that could be injected through the electrode would be about 5 $\mu C$, or 10 mA at a 0.5 ms pulse width.

A further refinement of such a device having a cathodic electrode configuration as shown on the right side of FIG. 5 is to allow individual contacts 212 to be selectively turned on or off. At any given current amplitude, this selective turning on or off allows all active contacts to be operating at maximum current density and thus maximum activation function magnitude. The active contacts would be distributed across the device surface so as to provide maximum coverage. For example, if the current amplitude were reduced by 50%, every other contact would be turned on. Another use of individual contact programmability would be to adjust the activation function and focus it at specific regions around the acupoint.

Yet a further refinement of the electrode configuration is to have individual voltage or current sources for groups of contacts as needed to manage different required amplitudes. For example, the cathode(s) on the top surface of the device could be stimulated at one amplitude while the cathode(s) on the bottom surface of the device could be stimulated at a different amplitude.

Figure 6:
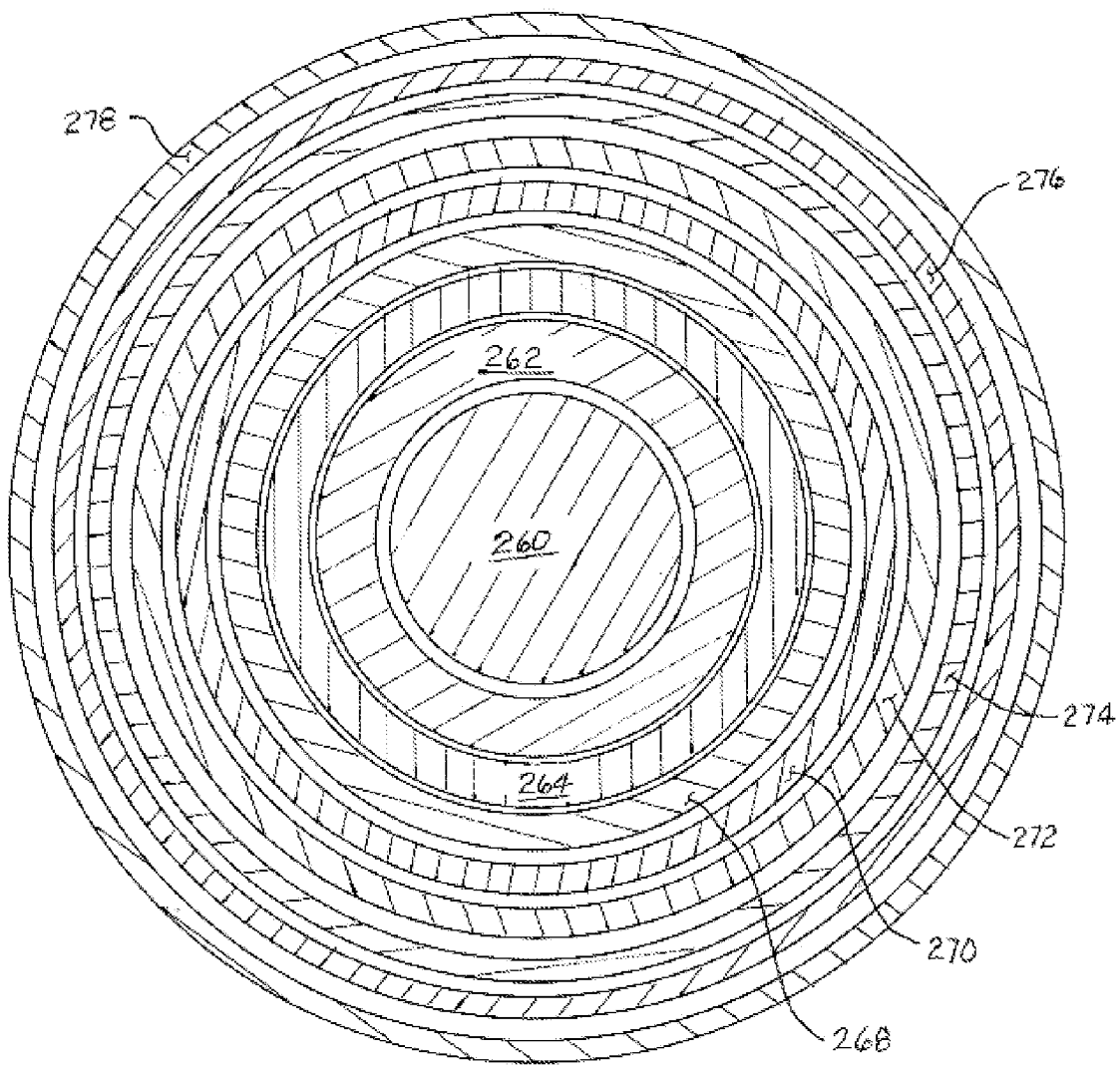
FIG. 6 shows concentric ring cathodic electrodes used to keep a stimulation current of varying amplitudes focused on a desired target acupoint.

Still a further refinement of the electrode configuration is to have an array of concentric cathodic ring electrodes with increasing diameters, as shown in FIG. 6. Such a configuration (which could be placed on both the top and bottom of the disc-shaped housing 200, or just on one of the top or bottom surface), allows the cathodic electrode surface area to vary with current amplitude while maintaining the electric field centered on the desired target acupoint.

As should be evident from the above description, the size of the electrode should not only be selected based on the amount of current that flows through the electrode surface, but also as a function of the purpose for which the electrode is being used. That is, while there is a theoretical benefit to having many small diameter contacts to activate fibers or tissue very close to the device, there is no benefit to having many small contacts for a single target tissue location, such as a nerve, that is further away. Additionally, a device intended to activate local subcutaneous fibers is better off with electrodes on both the top and bottom surfaces of the device. However, a device intended to a stimulate a single target tissue location some distance from the electrode is better off having the electrode contact only on the bottom surface of the device so that the stimulation can be focused at the desired stimulation site located underneath the electrode, as described below in connection with FIG. 11.

Thus, in summary, sometimes it is best to use large surface area electrodes, and sometimes it is best to use small surface area electrodes. Sometimes it is best to use electrodes on both the top and bottom surfaces of the stimulator device, and sometimes it is best to use electrodes only on the bottom surface (where the "bottom surface" is the surface facing the target tissue location located more than a few millimeters away from the electrode). Much depends on the purpose of the stimulation, and how far away the target stimulation location is from the electrode surfaces.

FIG. 6 depicts one preferred technique to have the electrode surface area vary with current amplitude while maintaining the electric field centered on the acupoint, or other target location. An inner circular electrode 260 is activated at the lowest current amplitude. As the amplitude of the stimulation current increases, additional ring electrodes are activated. Thus, for example, if increasing current amplitudes of I1, I2, I3, . . . I9 are to be used, wherein I1<I2<I3<I4 . . . <I9, then the inner circular electrode 260 is used for the lowest amplitude stimulation current I1. If current I2 is used, then circular electrodes 260 and ring 262 are used. If current I3 is used, then circular electrode 260 and ring electrodes 262 and 264 are used. If current I4 is used, then circular electrode 260 and ring electrodes 262, 264 and 268 are used. If current I5 is used, then circular electrode 260 and ring electrodes 262, 264, 268 and 270 are used. This process continues, with one more ring electrode being added to increase the current to the next value, until the maximum current I9 is used, which combines circular electrode 260 and ring electrodes 262, 264, 268, 270, 272, 274, 276 and 278.

Figure 7:
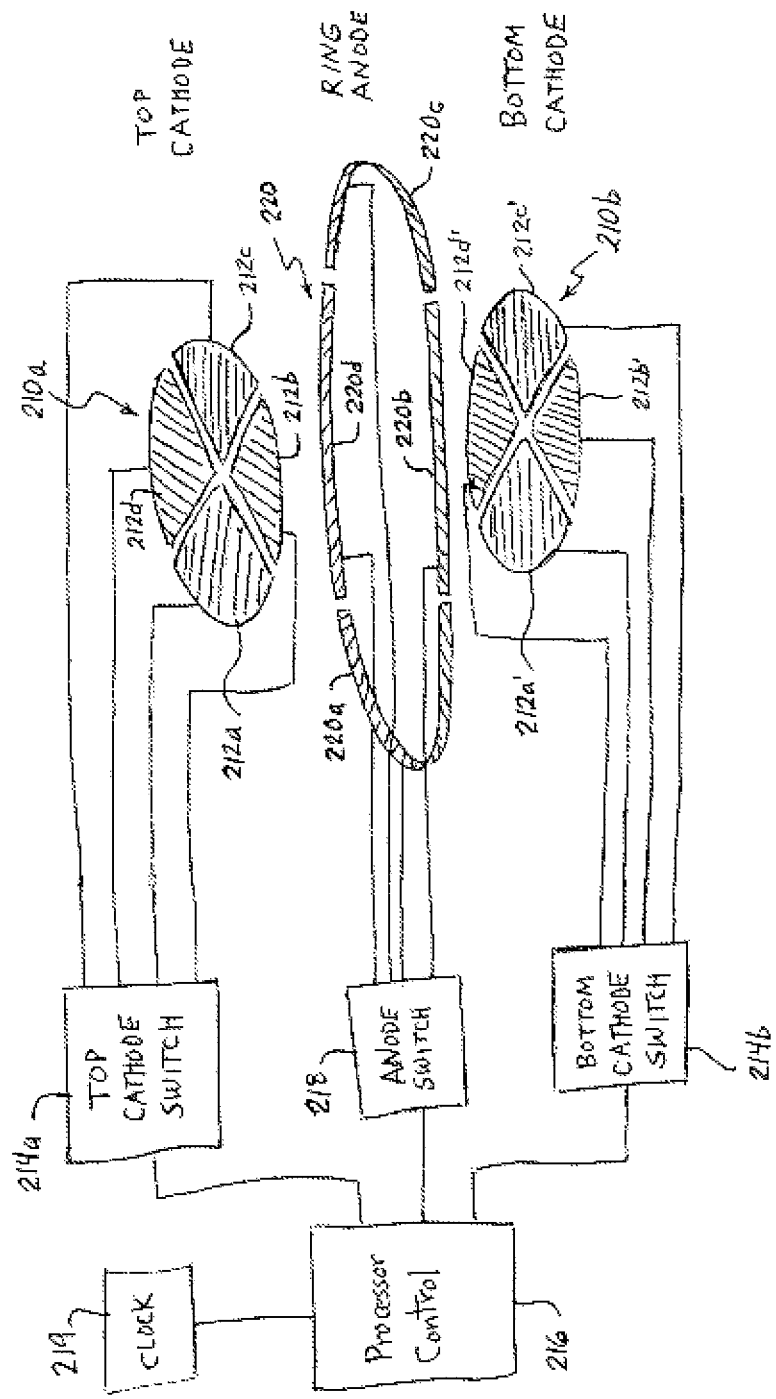
FIG. 7 diagrammatically and functionally illustrates how the cathodic and anodic electrodes used with a disc-shaped stimulator may be segmented or partitioned and operated with cathodic and anodic switching circuitry in order to better optimize the electrode surface area, thereby helping to better control the current density flowing through the electrodes so as to have the stimulation current more optimally penetrate body tissue surrounding the electrodes.

The ability to selectively use only a segment, or portion, of the available electrode surface area in order to maximize the current density, and thus maximize the ability to have the stimulation current better activate stimulated tissue, is illustrated diagrammatically and functionally in FIG. 7. As seen in FIG. 7, the top cathode electrode 210a is shown as being segmented into four separate cathode portions 212a, 212b, 212c and 212d. Each of these separate segments or portions may be individually energized (turned ON) through the functionally-illustrated Top Cathode Switch 214a, controlled by Processor 216. The Processor 216 (which is only functionally illustrated in FIG. 6) provides all the needed control signals for operation of the IEAD that allow it to generate a stream of stimulation pulses (see FIGS. 8 and 8A for a typical stimulation waveform and stimulation sad) in accordance with a specified stimulation regimen. The stimulation regimen may include energizing one of the four cathode electrode segments, or all of them (or two of them, or three of them) in order to obtain the desired density of the stimulus current that flows through the catheter electrode 210a.

In like manner, the bottom cathode electrode 210b is shown as being segmented into four separate cathode portions 212a, 212b, 212c and 212d. Each of these separate segments or portions may be individually energized (turned ON) through the functionally-illustrated Bottom Cathode Switch 214b, controlled by Processor 216. Hence, signals from the Processor 216 may selectively control which segments or portions of the cathode electrode 210b are energized, thereby allowing a desired density of the stimulus current flowing through the catheter electrode 210b to be achieved.

The ring anodic electrode 220 may similarly be divided into smaller portions or segments, 220a, 220b, 220c and 220d. These segments may be individually energized by the Anode Switch 218 so that only one segment in ON and three are OFF, two are ON and two are OFF, three are ON and one is OFF, or all four are ON. In this way, a desired density of the stimulus current flowing through the anode electrode 220 may be achieved.

It is to be noted that the segmentation of the TOP and BOTTOM Cathode electrodes 210a and 210b, as shown in FIG. 7, as well as the segmentation of the Anode electrode 220, also shown in FIG. 7, is intended to only be exemplary, and not limiting. That is, while four segments for each catheter electrode are illustrated, in practice, this could be any number of segments, or an array of smaller cathode electrodes, as shown, e.g., in FIGS. 4 and 5, or concentric ring cathodic electrodes as shown in FIG. 6 Similarly, while four segments or individual portions 220a, 220b, 220c and 220d of the Anode ring electrode 220 are shown, there could be any number of anode segments employed, as shown, e.g., in FIG. 4. The point is, both the top and bottom cathodic electrodes 210a and 210b, as well as the anodic electrode 220, may be selectively electrically divided into smaller electrode surface areas by controlling which segments, or portions, of the electrode's surface area are energized (where "energized" means electrically turned ON so that current flows through the electrode as controlled by the processor control circuit 216). This feature allows the current density present in the stimulus current to be better managed, which in turn allows for better control of which body tissue is activated by the stimulus current.

One preferred application for the IEAD disclosed herein is for the treatment of hypertension. For this application, an IEAD is fabricated so as to reside in a coin-sized housing having a diameter of approximately 22-24 mm, a thickness of approximately 2.2 to 2.5 mm, which size and shape is suitable for implantation at acupoint PC6 to a depth of between 3-5 mm. Such EA device is configured to continuously generate a charge balanced monophasic stimulation pulses, as diagrammatically illustrated in FIG. 8, having a pulse amplitude A1 of between 2 to 25 mA, a pulse width (PW), or T1, of between 0.2 to 0.6 msec (200 to 600 μsec), at a frequency of between 1 and 5 Hz (i.e., a period T2 which varies from 200 to 1000 msec) during a stimulation session that has a duration T3 of from 15 to 45 minutes (preferably about 30 minutes), which stimulation session is applied no more often than a time T4, where T4 may be, e.g., no more than twice a week and no less than once every other week (preferably once a week).

One of the reasons that acupoint P6 is selected for the application of electroacupuncture stimuli for the purpose of treating hypertension is because the median nerve is also at this location, about 5-6 mm below where the EA device is to be implanted (2-3 mm below the skin surface). This means that not only may the benefits for the favorable treatment of hypertension be obtained from applying classical acupuncture or electroacupuncture at this particular acupoint, but also the benefits for the favorable electrostimulation of the median nerve for the treatment of hypertension are obtained.

In order to effectively stimulate the median nerve where it is 5-6 mm below where the stimulation device is implanted, it is best for the anode to cathode center-to-center spacing to be at least twice this amount, or approximately 10-12 mm. If this is not the case, then the shunting of current between the anode and cathode may be too great. Advantageously, this criteria is satisfied well by having a radial ring anode electrode 220 (see, e.g., FIGS. 2, 3, and 3A) at the edge of a 22-24 mm diameter device.

In a specific configuration for treating, e.g., hypertension through application of EA stimulation pulses at acupoint P6, an IEAD is configured to generate a stimulus current having an amplitude of 15-20 mA or so. Pulses delivered are charge balanced monophasic passive recharge waveforms at 0.5 msec (500 μsec) delivered at up to 4 Hz (nominally 2 Hz) in 30 minute sessions once per week. The cathode 210, as shown in FIGS. 2, 3 and 3A, has a diameter of 2-3 mm, and is placed on the top and bottom surface of the disc-shaped housing 200. The anode 220 comprises a ring electrode 220 located at the perimeter of the disc-shaped housing 200.

SPECIFIC EXAMPLE

A specific example of an implantable electroacupuncture device (IEAD) will next be described in connection with the description of FIGS. 9-22. This description is presented only to illustrate and describe a specific example of an IEAD. This description is not intended to be exhaustive or to limit the invention to any precise form disclosed. Many modifications and variations are possible in light of the teachings presented herein.

Advantageously, the IEAD described in connection with this specific example comprises an implantable, self-contained, device powered by a small, thin, coin-cell type battery having an internal impedance of at least five ohms. While the device described is intended for, and is described for use as, an electroacupuncture (EA) device, or IEAD, it should be noted that it may be used for other similar tissue stimulation applications. Moreover, while the preferred EA device is leadless, for some applications a short lead may be needed to correctly position the electrodes precisely at a desired stimulation site.

In an exemplary embodiment, the EA device includes two electrode contacts mounted on or connected to the surface of its housing. The EA device is adapted to treat a particular disease or health condition of a patient. In one embodiment, the electrodes of the EA device are mounted on the surfaces of its housing and include a central cathode electrode on one side of the housing, and an annular anode electrode that surrounds the cathode. In another embodiment, the anode annular electrode is a ring electrode placed around the perimeter edge of a coin-shaped housing.

As indicated above, the preferred EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected target stimulation site, e.g., an acupuncture site ("acupoint") known to moderate or affect an identified health condition of a patient.

The EA device is easy to implant. Also, most embodiments are symmetrical. This means that there is no way that it can be implanted incorrectly (unless the physician puts it in up-side-down, which would be difficult to do given the markings on its case). All that need be done is to cut the incision, and slide the device in place through the incision. Once the implant pocket has been prepared, it is as easy as sliding a coin into a slot.

Such implantation can usually be completed in less than 10 minutes in an outpatient setting, or in a doctor's office. Only minor, local anesthesia need be used. No major or significant complications are envisioned for the implant procedure. The EA device can also be easily and quickly explanted, if needed or desired.

The EA device is self-contained. It includes a primary battery to provide its operating power. Such primary battery has a high impedance, greater than 5 ohms. In view of such high impedance, the EA device includes battery control circuitry that limits the amount of instantaneous current drawn from the primary battery to prevent excessive voltage drops in the output voltage of the battery. Such battery control circuitry carefully manages the delivery of power by the EA device so as to allow the device to perform its intended function for several years.

Once the EA device is implanted in a patient, the patient should not even know it is there, except for a slight tingling that may be felt when the device is delivering bursts of stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected target stimulation site, e.g., a specified acupoint, are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's medical condition.

The EA device is, compared to most implantable medical devices, relatively easy to manufacture and uses few components. This not only enhances the reliability of the device, but keeps the manufacturing costs low, which in turn allows the device to be more affordable to the patient.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

A key feature included in the design of the EA device is the use of a commercially-available battery as its primary power source. A preferred commercially-available battery to use in the EA device is a small, thin, disc-shaped battery, also known as a "coin cell" battery, such as the 3 V CR1612 lithium battery available from Panasonic, or equivalents thereof. Such coin-cell batteries are quite common and readily available for use with most modern hand-held electronic devices.

Coin-cell type batteries come in many sizes, and employ various configurations and materials. However, insofar as the inventors or Applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible. Further, because of the high internal impedance, dips in the battery output voltage (caused by any sudden surge in instantaneous battery current) may occur that could compromise the performance of the device. Additionally, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Advantageously, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture and to provide the device to patients at an affordable cost.

Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05× 23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, an important aspect of the invention recognizes that an electroacupuncture modulation scheme, or other tissue stimulation scheme, need not be continuous, thereby allowing the implanted device to use a small, high density, power source to provide such non-continuous modulation. (Here, it should be noted that "modulation," as that phrase is used herein, is the application of electrical stimulation pulses, at low intensities, low frequencies and low duty cycles, to at least one of the target stimulation sites, e.g., an acupuncture site that has been identified as affecting a particular condition of a patient.) As a result, the device can be very small. And, because the electrodes typically form an integral part of the housing of the device, the device may thus be implanted directly at (or very near to) the desired target tissue location.

Mechanical Design

Figure 9:
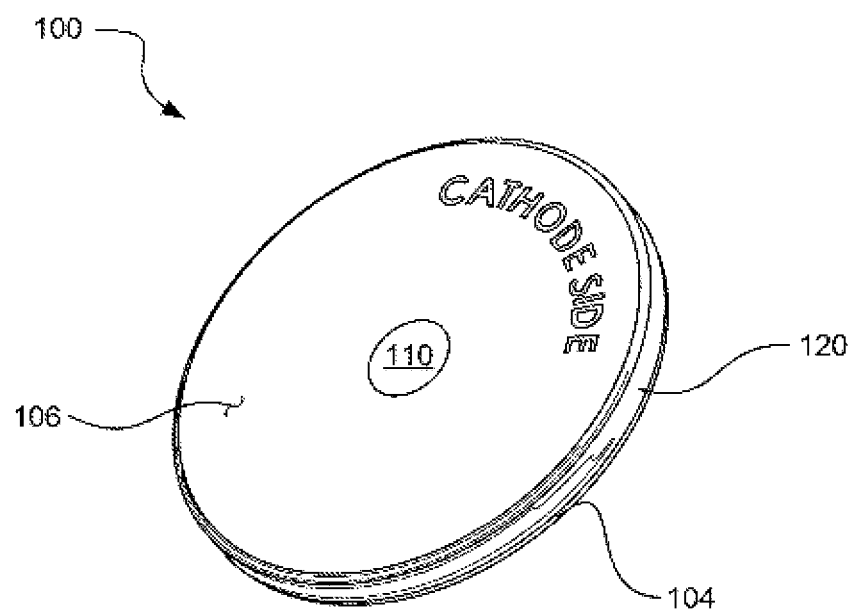
FIG. 9 is a perspective view of a preferred implementation of an implantable electroacupuncture device (IEAD) made in accordance with the teachings presented herein.

Turning to FIG. 9, a small, implantable, electroacupuncture device (IEAD) is shown in perspective view. Such device is designed to be used to treat a disease, deficiency, or other medical condition of a patient. The IEAD 100 may also sometimes be referred to as an implantable electroacupuncture stimulator (IEAS). As seen in FIG. 9, the IEAD 100 has the appearance of a disc or coin, having a front side 106 (which is also labeled as the "Cathode Side"), a back side (also referred to as the "Skin Side") 102 (which skin side is not visible in FIG. 1) and an edge side 104.

As used herein, the "front" side of the IEAD 100 is the side that is positioned so as to face the target stimulation point (e.g., the desired acupoint) where EA stimulation is to be applied when the IEAD is implanted. The "back" side is the side opposite the front side and is the farthest away from the target stimulation point when the IEAD is implanted, and is usually the side closest to the patient's skin. The "edge" of the IEAD is the side that connects or joins the front side to the back side. In FIG. 1, the IEAD 100 is oriented to show the front side 102 and a portion of the edge side 104.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 17, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 17:
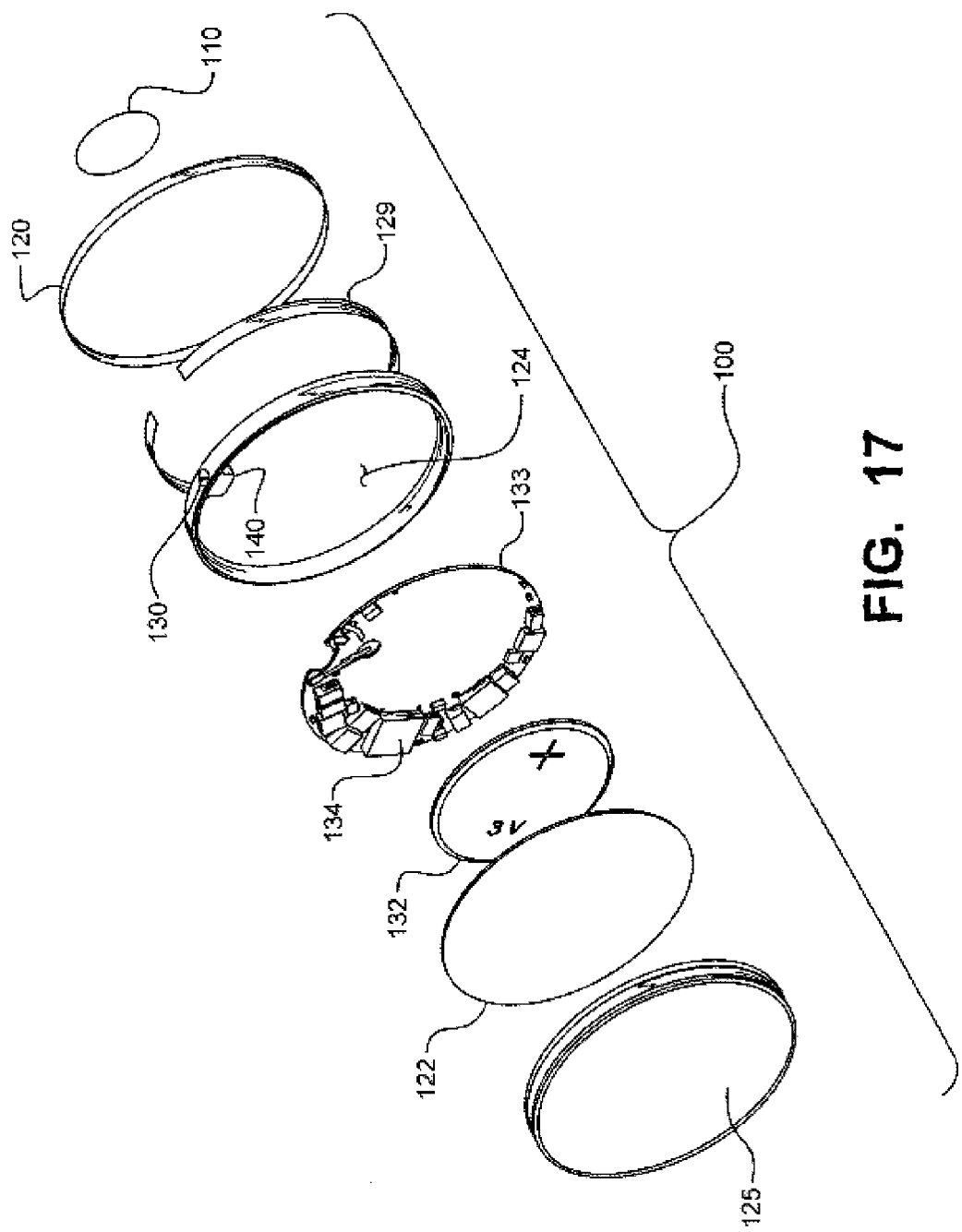
FIG. 17 is an exploded view of the IEAD assembly, illustrating its constituent parts.

The embodiment of the IEAD 100 shown in FIG. 9 utilizes two electrodes, a cathode electrode 110 that is centrally positioned on the front, or "cathode," side 106 of the IEAD 100, and an anode electrode 120. The anode electrode 120 is a ring electrode that fits around the perimeter edge 104 of the IEAD 100. Not visible in FIG. 9, but which is described hereinafter in connection with the description of FIG. 17, is a layer of insulating material 129 that electrically insulates the anode ring electrode 120 from the perimeter edge 104 of the housing or case 124.

Not visible in FIG. 9, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 15, 15A, 15B and 17.

In contrast to the feed-through pin that establishes electrical contact with the anode electrode, electrical connection with the cathode electrode 110 is established simply by forming or attaching the cathode electrode 110 to the front surface 106 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 17), except for the outside surface of the anode ring electrode 120 and the cathode electrode 110.

One significant advantage of this electrode configuration is that it is symmetrical. That is, when implanted, the surgeon or other medical personnel performing the implant procedure, need only assure that the cathode side of the IEAD 100, which (for the embodiment shown in FIGS. 9-17) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 10:
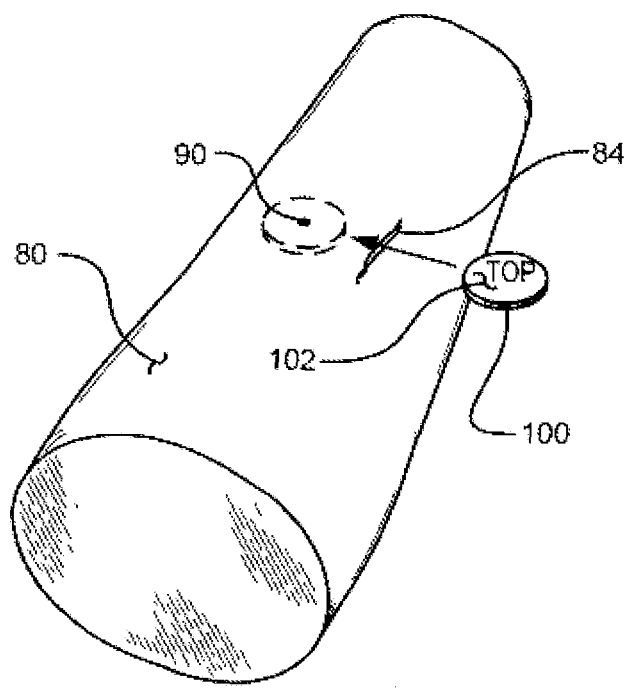
FIG. 10 illustrates the location of an exemplary target tissue stimulation site, e.g., an acupoint, whereat the IEAD of FIG. 9 may be implanted for the treatment of a particular disease or condition.

FIG. 10 illustrates the location of an exemplary target stimulation acupoint, e.g. acupoint PC6 located on the patient's wrist, whereat the IEAD of FIG. 9 may be implanted for the treatment of a particular disease or condition of the patient, e.g., hypertension. Such location is representative of a wide variety of acupoints, or other target tissue locations, whereat the IEAD of FIG. 9 could be implanted.

Figure 11:
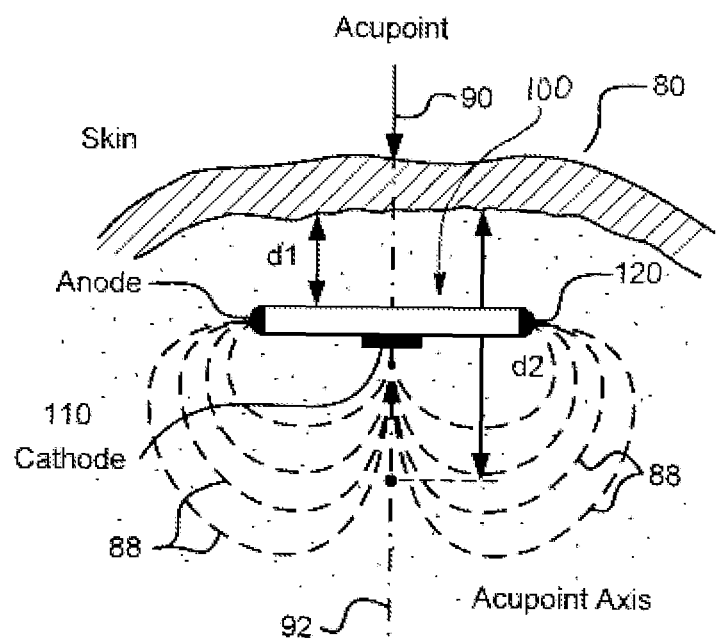
FIG. 11 shows a sectional view of an IEAD implanted at a selected target stimulation site, and illustrates the electric field gradient lines created when an electroacupuncture (EA) pulse is applied to the tissue through the central electrode and ring electrode attached to the bottom surface and perimeter edge, respectively, of the IEAD housing.

An implanted IEAD 100 is illustrated generally in FIG. 11, and the manner of implanting the IEAD 100 is illustrated in FIG. 10. FIG. 11 shows a sectional view of a limb 80 of the patient wherein an acupoint 90 (e.g., acupoint PC6) has been identified that is to receive acupuncture treatment (in this case electroacupuncture treatment). An incision 84 (shown in FIG. 10) is made into the limb 80 a short distance, e.g., 10-15 mm, away from the acupoint 90. A slot (parallel to the limb) is formed at the incision by lifting the skin closest to the acupoint up at the incision. As necessary, the surgeon may form a pocket under the skin at the acupoint location. The IEAD 100, with its top side 102 being closest to the skin (and thus also referred to as the "Skin Side"), is then slid through the slot 84 into the pocket so that the center of the IEAD is located under the acupoint 90 on the skin surface. This implantation process is as easy as inserting a coin into a slot. With the IEAD 100 in place, the incision 84 is sewn or otherwise closed, leaving the IEAD 100 under the skin 80 at the location of the acupoint 90 where electroacupuncture (EA) stimulation is desired (shown in FIG. 11).

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth d2 (see FIG. 11) that varies depending on the particular acupoint location. When stimulation is applied at the target tissue point, such stimulation is effective at treating a selected condition of the patient, e.g., high cholesterol, because there is something in the tissue at that location, or near that location, such as a nerve, a tendon, a muscle, or other type of tissue, that responds to the applied stimulation in a manner that contributes favorably to the treatment of the condition experienced by the patient.

FIG. 11 illustrates a sectional view of the IEAD 100 implanted so as to be centrally located under the skin at the selected acupoint 90, and over the acupoint axis line 92. Usually, for most patients, the IEAD 100 is implanted at a depth d1 of approximately 2-4 mm under the skin. The top (skin) side 102 of the IEAD is nearest to the skin of the limb 80 of the patient. The bottom (cathode) side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 11 further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 12 shows a plan view of the "front" (or "cathode") side 106 of the IEAD 100. As seen in FIG. 12, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 12A shows a side view of the IEAD 100. The ring anode electrode 120, best seen in FIG. 12A, has a width W1 of about 1.0 mm, or approximately ½ of the width W2 of the IEAD.

FIG. 13 shows a plan view of the "back" (or "skin") side of the IEAD 100. As will be evident from subsequent figure descriptions, e.g., FIGS. 15A and 15B, the back side of the IEAD 100 comprises a cover plate 122 that is welded in place once the bottom case 124 has all of the electronic circuitry, and other components, placed inside of the housing.

FIG. 13A is a sectional view of the IEAD 100 taken along the line A-A of FIG. 13. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 13A further illustrates how the cover plate 122 is welded, or otherwise bonded, to the bottom case 124 in order to form the hermetically-sealed IEAD housing 100.

Figure 14:
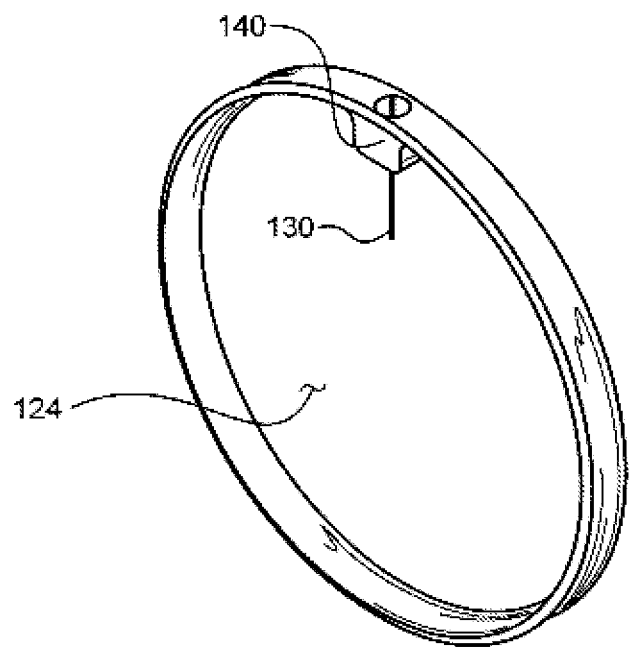
FIG. 14 is a perspective view of the IEAD housing, including a feed-through pin, before the electronic components are placed therein, and before being sealed with a cover plate.

FIG. 14 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 14A:
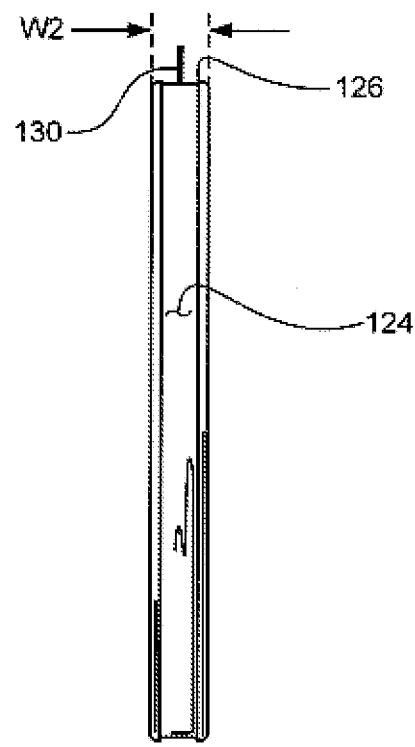
FIG. 14A is a side view of the IEAD housing of FIG. 14.

FIG. 14A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 17) is placed between the backside of the ring anode electrode 120 and the perimeter edge of the case 124 where the ring anode electrode 120 is placed around the edge of the case 124.

FIG. 15 shows a plan view of the empty IEAD case 124 shown in the perspective view of FIG. 14. An outline of the recess cavity 140 is also seen in FIG. 15, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 15 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 15A depicts a sectional view of the IEAD housing 124 of FIG. 15 taken along the section line A-A of FIG. 15. FIG. 15B shows an enlarged view or detail of the portion of FIG. 15A that is encircled with the line B. Referring to FIGS. 15A and 15B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 15A and 15B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 14A, 15, 15A and 15B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 16, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 14 and FIG. 15.

FIGS. 16A and 16B show a plan view and side view, respectively, of the electronic assembly 133 shown in FIG. 16. The electronic components are assembled and connected together so as to perform the circuit functions needed for the IEAD 100 to perform its intended functions. These circuit functions are explained in more detail below under the sub-heading "Electrical Design". Additional details associated with these functions may also be found in Applicant's Parent Application, referenced above in Paragraph [0001].

FIG. 17 shows an exploded view of the complete IEAD 100, illustrating its main constituent parts. As seen in FIG. 17, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby or alumina insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 17, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 17 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 17 is a layer of silicon molding 125 that is used to cover all surfaces of the entire IEAD 100 except for the anode ring electrode 120 and the circular cathode electrode 110. An overmolding process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with the specific example described in FIGS. 9, and 12-17. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

FIG. 17A schematically illustrates a few alternative electrode configurations that may be used with the invention. The electrode configuration schematically shown in the upper left corner of FIG. 17A, identified as "I", schematically illustrates one central electrode 110 surrounded by a single round ring electrode 120. This is one of the preferred electrode configurations that has been described previously in connection, e.g., with the description of FIGS. 9, 10, 11 and 17, and is presented in FIG. 17A for reference and comparative purposes.

In the lower left corner of FIG. 17A, identified as "II", an electrode/array configuration is schematically illustrated that has a central electrode 310 of a first polarity surrounded by an oval-shaped electrode array 320a of two electrodes of a second polarity. (This oval-shaped array 320a could also be round.) When the two electrodes (of the same polarity) in the electrode array 320a are properly aligned with the body tissue being stimulated, e.g., aligned with a nerve underlying the desired acupoint, then such electrode configuration can stimulate the body tissue (e.g., the underlying nerve) at or near the desired acupoint(s) with the same, or almost the same, efficacy as can the electrode configuration I (upper right corner of FIG. 17A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 17A, identified as "III", en electrode configuration is schematically illustrated that has a round central electrode/array 310b of three electrode segments of a first polarity surrounded by an electrode array 320b of three electrode segments of a second polarity. (These round or oval shapes could be altered, as desired or needed. That is, the round central electrode/array 310b could be an oval-shaped electrode array, and the oval-shaped electrode array 320b could be a round electrode array.) As shown in configuration III of FIG. 17A, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 17A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310c are likewise arranged symmetrically in a round or oval-shaped array. While preferred for many configurations, the use of a symmetrical electrode/array, whether as a central electrode array 310 or as a surrounding electrode/array 320, is not always required.

The electrode configurations I, II, III and IV shown schematically in FIG. 17A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, . . . n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

As has already been mentioned, the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are illustrated in Appendix A and Appendix B.

Electrical Design

Next, with reference to specific example presented in connection with FIGS. 18-22, the electrical design and operation of the circuits employed within the implantable electroacupuncture device (IEAD) 100 will be described. Such circuits advantageously allow a relatively inexpensive, thin, high impedance, coin-cell type battery to be employed within the IEAD to provide its operating power for the IEAD over a long period of time. More details associated with the design of the electrical circuits described herein may be found in Applicant's previously-filed Parent Application, referenced in Paragraph [0001].

Figure 18:
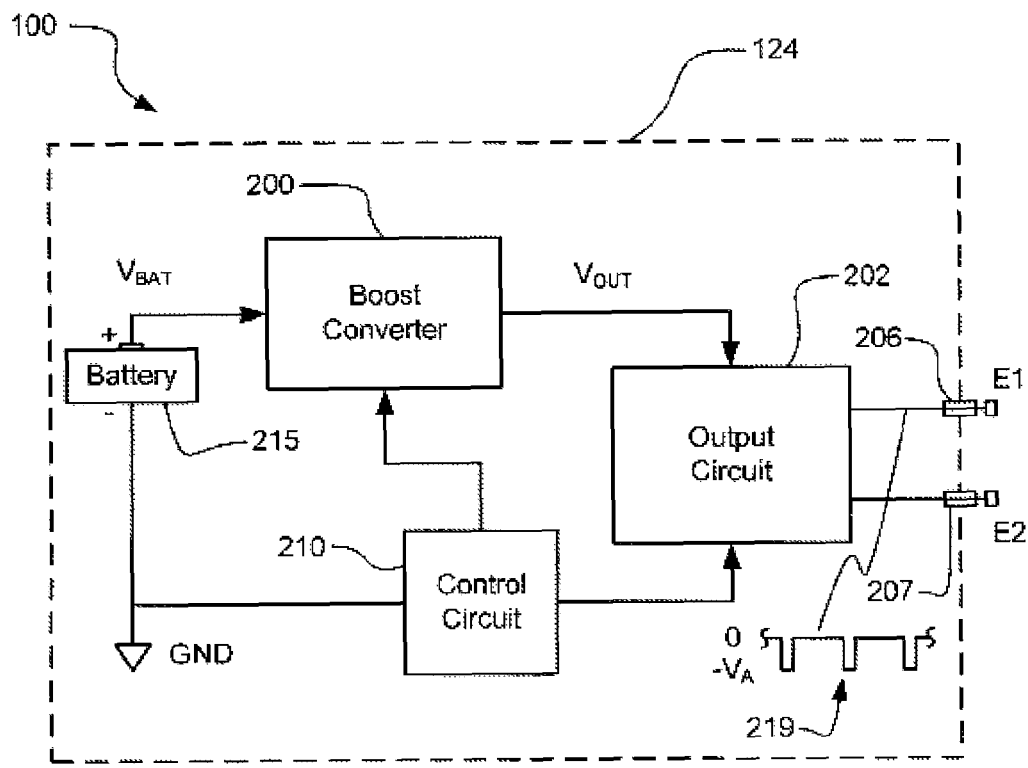
FIG. 18 illustrates a functional block diagram of the electronic circuits used within an IEAD of the type described herein.

FIG. 18 shows a functional block diagram of an IEAD 100 made in accordance with the teachings disclosed herein. As seen in FIG. 18, the IEAD 100 uses an implantable battery 215 having a battery voltage $V_{BAT}$. In one preferred embodiment, this battery 215 comprises a lithium battery having a nominal output voltage of 3 V, such as the CR1612 battery manufactured by Panasonic. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 8:
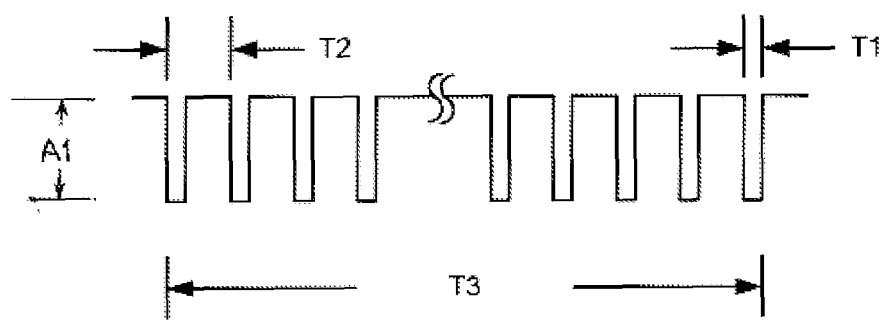
FIG. 8 is a waveform timing diagram that illustrates a typical monophasic stimulation pulse, showing what is meant by the terms pulse width, amplitude and frequency of stimulation, and therefore illustrates a timing waveform diagram of representative stimulation pulses generated during a stimulation session.
Figure 8A:
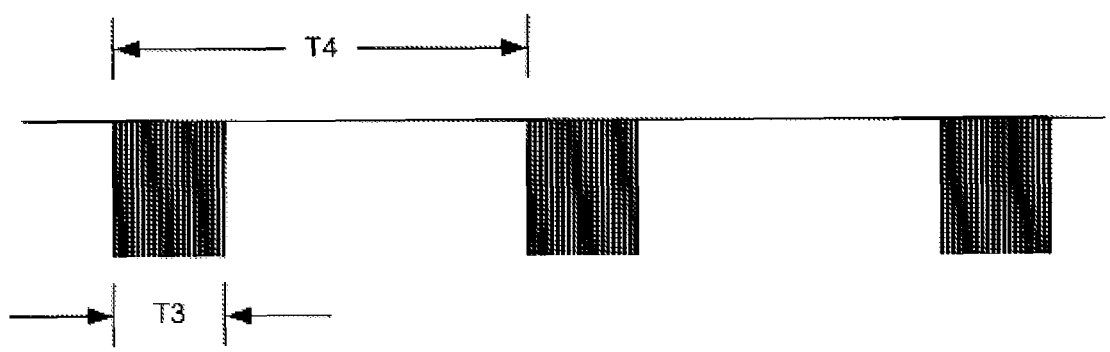
FIG. 8A shows a timing waveform diagram of multiple stimulation sessions, and thus illustrates the waveforms of FIG. 8 on a more condensed time scale.

As illustrated in the timing waveform diagrams of FIGS. 8 and 8A, a typical stimulation regimen comprises a continuous stream of stimulation pulses having a fixed amplitude, A1 (which may be expressed in voltage or current), a fixed pulse width T1, e.g., 0.5 millisecond, and at a fixed frequency f1, e.g., 2 Hz (where the frequency f1 is the inverse of the stimulation period T2, or f1=1/T2), during each stimulation session. The stimulation session, also as part of the stimulation regimen, has a duration T3, and is generated at a very low duty cycle, e.g., for 30 minutes once each week. The frequency of the stimulation sessions occurs once every T4 minutes. For example, if the duration of the stimulation session is 30 minutes, or T3=30 minutes, then T4 defines how often (or how infrequently) a stimulation session lasting T3 minutes occurs. Typically, the time T4 will be at least 24 hours (which is 1440 minutes), and may be as long as 20,160 minutes (2 weeks), and typically will be on the order of 10,080 minutes (1 week). Other stimulation regimens may also be used, e.g., using a variable frequency for the stimulus pulse during a stimulation session rather than a fixed frequency. Also, the rate of occurrence of the stimulation session may be varied, e.g., particularly at startup, so that T4 initially starts as short as, e.g., 1 day, and gradually ramps over a period of one or two weeks to a value as long as, e.g., 14 days.

In the specific example described here, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 18.

Thus, in the embodiment described in FIG. 18, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 18, and packaged as described above in connection with FIGS. 9-17, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny coin-cell type battery inside of the coin-sized stimulator provides enough energy for the stimulator to carry out its specified stimulation regimen over a period of several years, despite the fact that the battery typically has a relatively high battery impedance, e.g., greater than 5 ohms, and often as high as 150 ohms, or more. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 19:
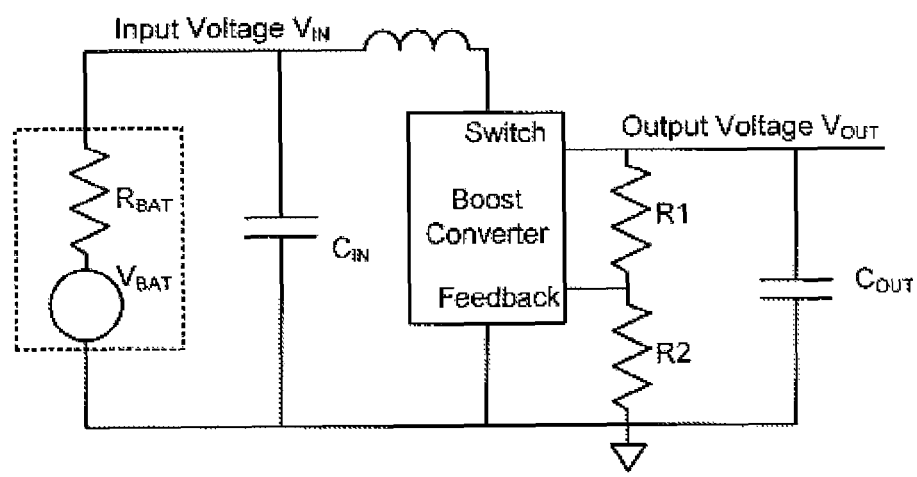
FIG. 19 functionally shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 19. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electro-acupuncture device.

In the boost converter circuit example shown in FIG. 19, the battery is modeled as a voltage source with a simple series resistance. With reference to the circuit shown in FIG. 19, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 19A, where the horizontal axis is time, and the vertical axis on the left is voltage, and the vertical axis of the right is current.

Figure 19A:
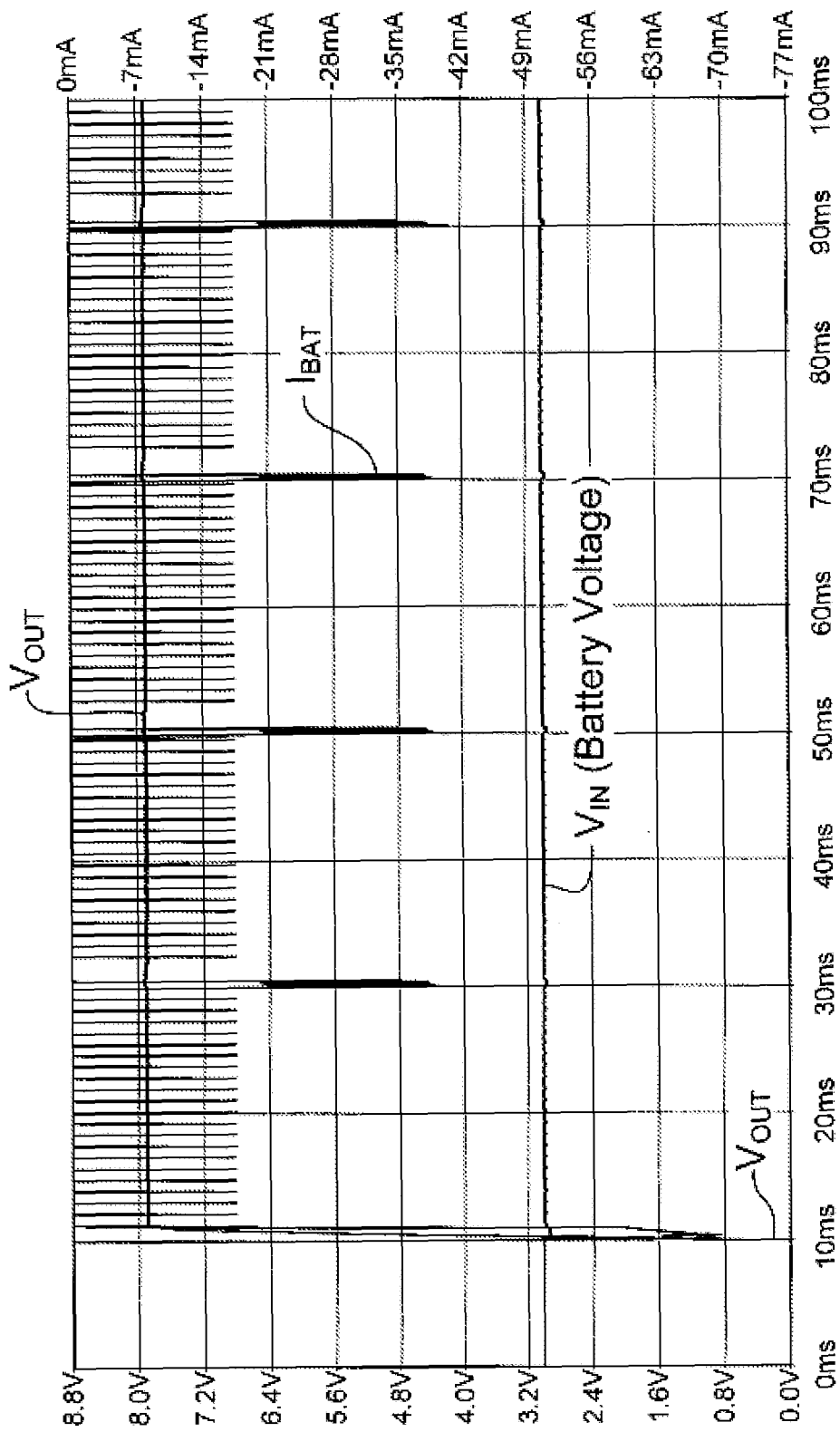
FIG. 19A illustrates a typical voltage and current waveform for the circuit of FIG. 19 when the battery impedance $R_{BAT}$ is small.

Referring to the waveform in FIG. 19A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 19B:
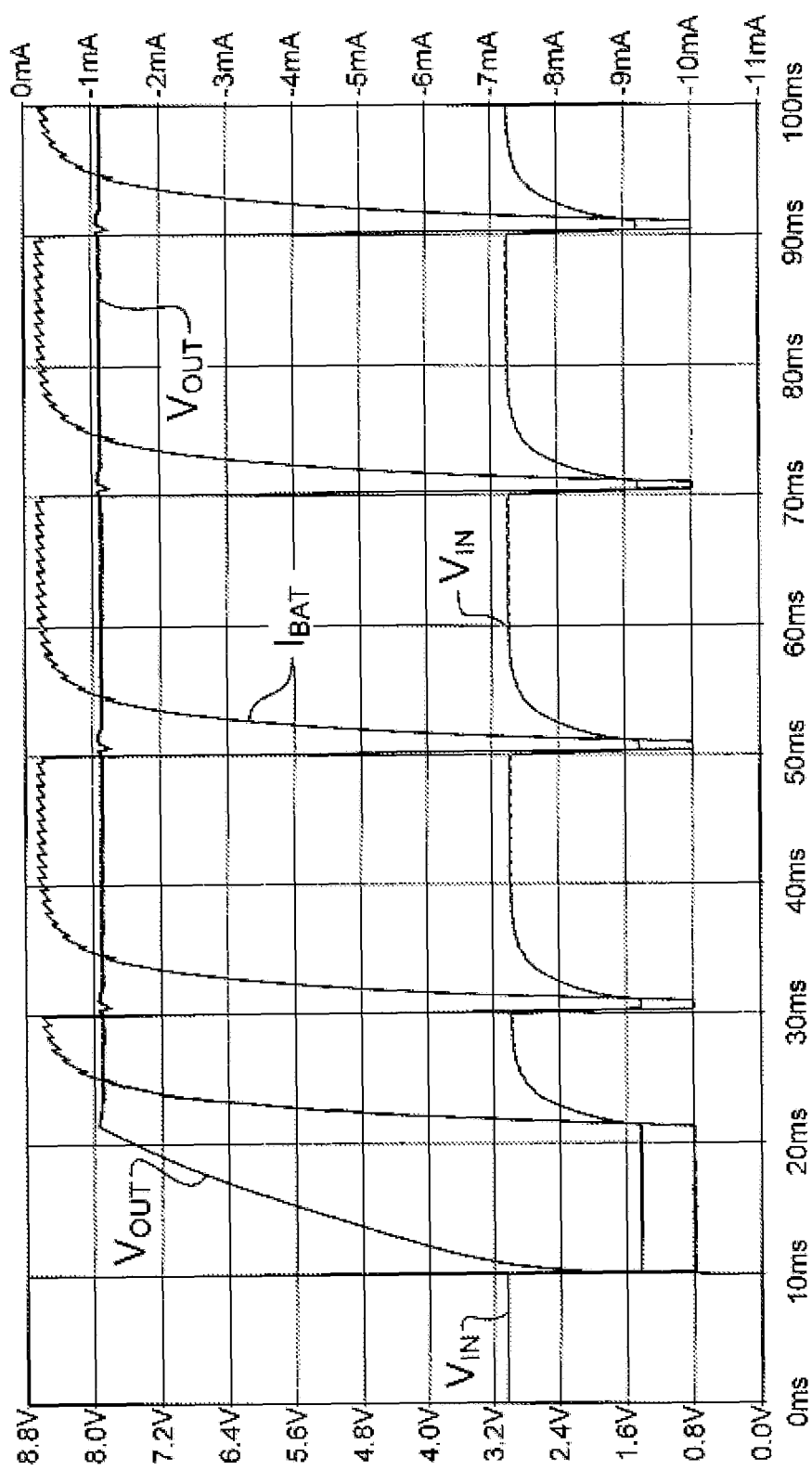
FIG. 19B shows the voltage and current waveform for the circuit of FIG. 19 when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 19B. In FIG. 19B, as in FIG. 19A, the horizontal axis is time, the left vertical axis is voltage, and the right vertical axis is current.

As seen in FIG. 19B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are not acceptable in any type of circuit except an uncontrolled oscillator circuit.

Also, it should be noted that although the battery used in the boost converter circuit is modeled in FIG. 19 as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when stimulation pulses are generated.

Figure 20:
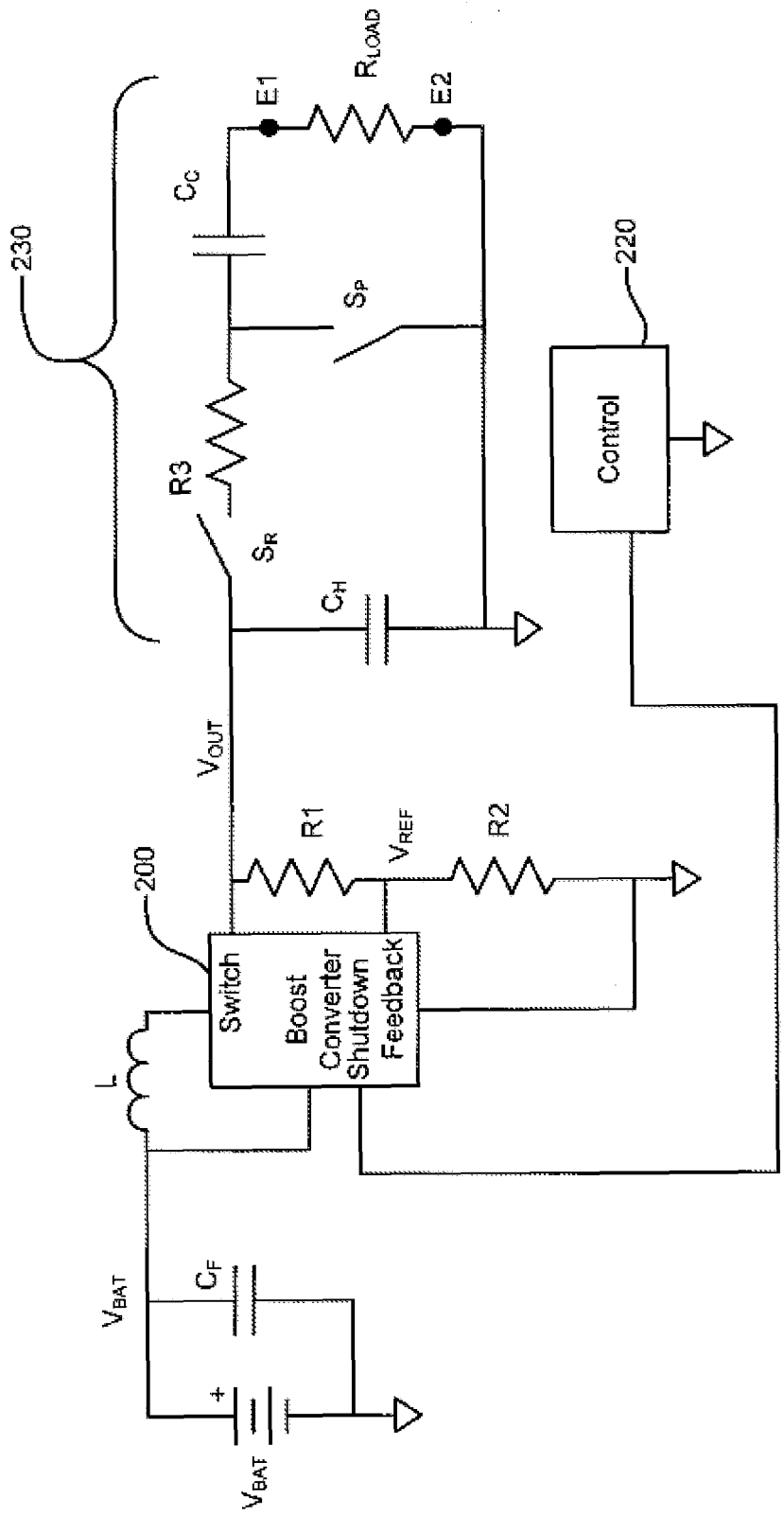
FIG. 20 shows one preferred boost converter circuit and a functional pulse generation circuit configuration for use within the IEAD.

To provide this needed current management, the IEAD 100 disclosed herein employs electronic circuitry as shown in FIG. 20, or equivalents thereof. Similar to what is shown in FIG. 18, the circuitry of FIG. 20 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

A variation of the above-described use of a digital control signal to duty cycle the boost converter circuit 200 ON and OFF is to let the digital control be generated within the boost converter 200 itself (without having to use a separate control circuit 220). In accordance with this variation, the boost converter circuit 200 shuts itself down whenever the battery voltage falls below a predetermined level above that required by the remaining circuitry. For example, the MAX8570 boost converter IC, commercially available from Maxim, shuts down when the applied voltage falls below 2.5 V. This is still a high enough voltage to ensure the microprocessor and other circuitry remain operational. Thus, as soon as the input voltage drops below 2.5 volts, the boost converter circuit shuts down, thereby limiting the instantaneous current drawn from the battery. When the boost converter shuts down, the instantaneous battery current drawn from the battery is immediately reduced a significant amount, thereby causing the input voltage to increase. The boost converter remains shut down until the microprocessor (e.g., the circuit U2 shown in FIG. 21, described below), and/or other circuitry used with the boost converter, determine that it is time to turn the boost converter back ON. Once turned ON, the boost converter remains ON until, again, the input voltage drops to below 2.5 volts. This pattern continues, with the boost converter being ON for a short time, and OFF for a much longer time, thereby controlling and limiting the amount of current that can be drawn from the battery. 2

In the circuitry shown in FIG. 20, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 20, $V_{REF}$ is proportional to the output voltage $V_{OUT}$, as determined by the resistor dividing network of R1 and R2.

The switches $S_P$ and $S_R$, shown in FIG. 20 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 20, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 20). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

It is also seen that in a variation of the embodiment shown in FIG. 20, a boost converter circuit 200 is used that shuts itself down whenever the input voltage falls below a prescribed threshold, e.g., 2.5 V. The boost converter remains shut down until other circuitry used with the boost converter determines that it is time to turn the boost converter back ON, e.g., whenever the feedback signal indicates the output voltage $V_{OUT}$ has fallen below a prescribed threshold, and/or whenever a prescribed period of time has elapsed since the last stimulus pulse was generated.

Figure 21:
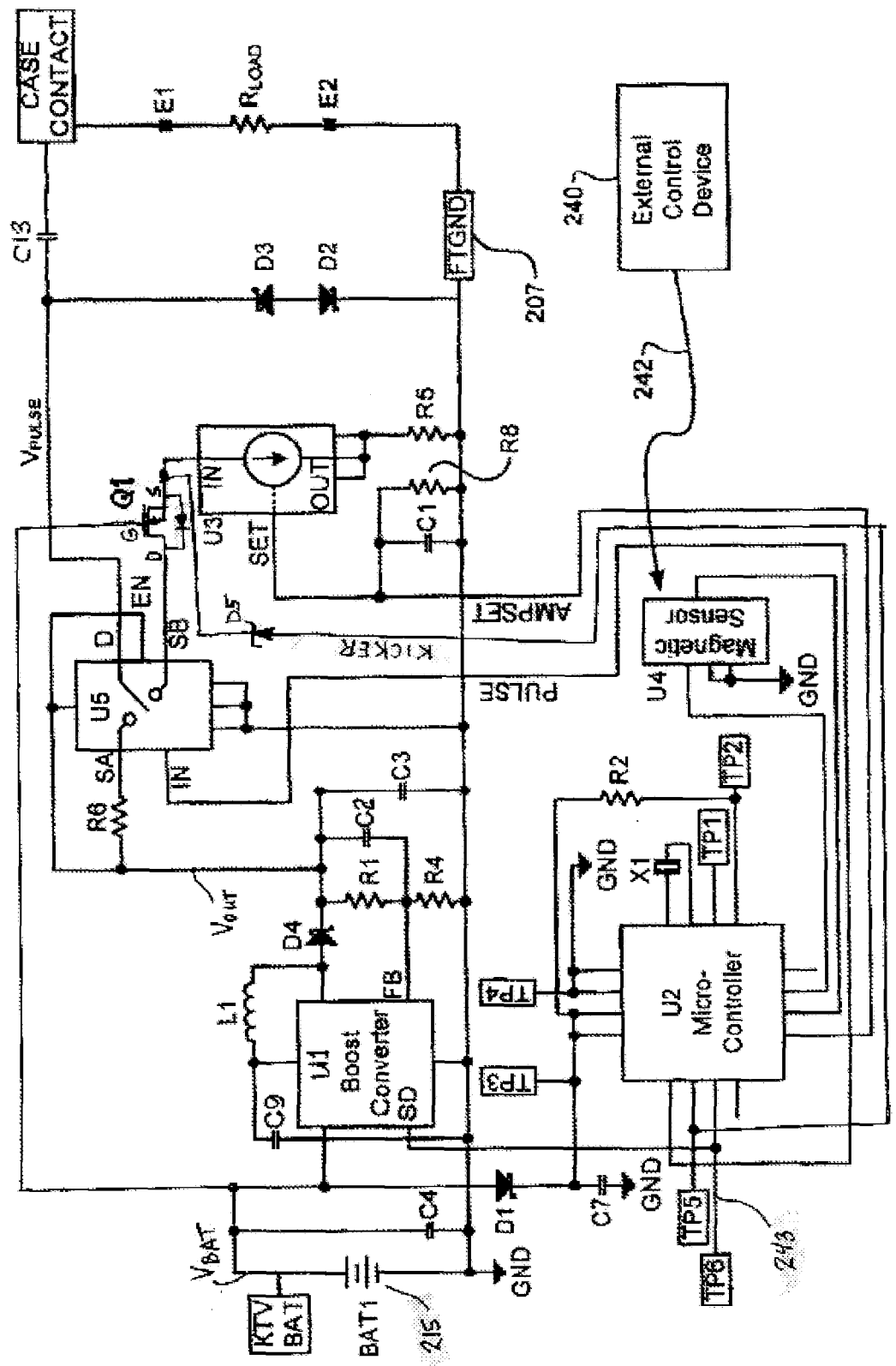
FIG. 21 depicts one preferred schematic configuration for an IEAD that utilizes a boost converter circuit U1, micro-controller circuit U2, programmable current source U3, sensor U4 and switch circuit U5 in order to perform the functions illustrated in the functional diagrams of FIGS. 7, 18, 19 and 20.

One preferred circuit implementation of the embodiment of the circuitry shown in FIG. 20 is shown in the schematic diagram presented in FIG. 21. That is, the circuitry depicted in the schematic diagram of FIG. 21 performs all of the functions illustrated in connection with the functional circuitry illustrated in FIG. 20. Additionally, the circuitry shown In FIG. 21 provides a few other additional features not necessarily evident from the functional diagram of FIG. 20, but which features nonetheless contribute to the overall utility and functionality of the IEAD circuitry shown in FIG. 21.

There are five integrated circuits (ICs) used as the main components of the IEAD circuitry shown in FIG. 21. The IC U1 is a boost converter circuit, and performs the function of the boost converter circuit 200 described previously in connection with FIGS. 19 and 20.

Still referring to FIG. 21, the IC U2 is a micro-controller IC and is used to perform the function of the control circuit 210 described previously in connection with FIG. 18, or the control circuit 220 described previously in connection with FIG. 20. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, which five parameters are clearly evident from the timing waveform diagrams of FIGS. 8 and 8A, and their accompanying descriptions. This allows the programming features of the micro-controller to be carried out in a simple and straightforward manner.

The micro-controller U2 primarily performs the function of generating the digital signal (when used) that shuts down the boost converter circuit to prevent too much instantaneous current from being drawn from the battery $V_{BAT}$, or performs other functions related to controlling and managing the power consumed within the IEAD 100. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drop across the switch U5 and current source U3.

It is important that the circuitry used in the IEAD 100, e.g., the circuitry shown in FIG. 20 or 21, or equivalents thereof, have some means for controlling the stimulation current that flows through the load, $R_{LOAD}$, which load may be characterized as the patient's tissue impedance at and around the acupoint or other target location that is being stimulated. This tissue impedance may typically vary from between about 300 ohms to 2000 ohms. Moreover, it not only varies from one patient to another, but it varies over time for the same patient. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 21, is one way to satisfy this need.

Still referring to FIG. 21, a fourth IC U4 is connected to the micro-controller U2. For the embodiment shown in FIG. 21, the circuit U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 21 by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth. Various other coding schemes that could be employed for this purpose are described in Applicant's Parent Application, referenced above in Paragraph [0001].

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Additional features associated with the use and operation of the circuitry of FIG. 21 which are not included through operation of the functional circuitry shown in FIG. 20, relate to the inclusion of a Schottky diode D4 at the output terminal LX of the boost convertor circuit U1 and the inclusion of a fifth integrated circuit (IC) U5, which circuit U5 essentially performs the same function as the switches $S_R$ and $S_P$ shown in FIG. 20.

The Schottky diode D4 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 21 is designed, the output voltage $V_{OUT}$ is designed to be nominally 15 volts (and could be as high as 25 volts) using a battery that has a nominal battery voltage of only 3 volts.

The inclusion of the fifth IC U5 in the circuit shown in FIG. 21 is, as indicated, used to perform the function of a switch. More particularly, the IC U5 shown in FIG. 21 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

The schematic diagram of FIG. 21, which shows the circuit implementation used within the IEAD 100, further includes a boost converter circuit U1 that is modulated ON and OFF using digital control generated within the boost converter circuit U1 itself. In accordance with this implementation, as explained briefly previously, the boost converter circuit 200 shuts itself down whenever the battery voltage falls below a predetermined level above that required by the remaining circuitry. For example, in the embodiment shown in FIG. 21, the boost converter circuit U1 is realized using a MAX8570 boost converter IC, commercially available from Maxim, or equivalents thereof. This particular boost converter IC shuts down when the applied voltage, $V_{BAT}$, falls below 2.5 V. Advantageously, a battery voltage of 2.5 volts is still a high enough voltage to ensure the microcontroller IC U2, and other circuitry associated with the operation of the IEAD 100, remain operational.

Thus, in operation, as soon as the battery voltage drops below 2.5 volts, the boost converter circuit U1 shuts down, thereby limiting the instantaneous current drawn from the battery. When the boost converter U1 shuts down, the instantaneous battery current drawn from the battery is immediately reduced a significant amount, thereby causing the battery voltage $V_{BAT}$ to increase.

As the battery voltage $V_{BAT}$ increases, the boost converter circuit U1 remains shut down until the microcontroller U2 determines that it is time to turn the boost converter back ON. This turn ON typically occurs in one of two ways: (1) just prior to the delivery of the next stimulus pulse, a turn ON signal may be applied to the Shutdown ("SD") terminal, signal line 243, of the boost converter circuit U1; or (2) as soon as the battery voltage, $V_{BAT}$, has increased a sufficient amount, as sensed at the feedback terminal FB of the boost converter circuit U1, the circuits within the boost converter circuit U1 are automatically turned back ON, allowing the output voltage $V_{OUT}$ to build up to a voltage level needed by the switch circuit U5 and the current source circuit U3 to generate an output stimulus pulse of the desired amplitude when the next PULSE signal is applied to the IN terminal of the switch U5 by the microcontroller U2.

Once turned ON, the boost converter remains ON until, again, the input voltage drops below 2.5 volts. This pattern continues, with the boost converter being ON for a short time, and OFF for a much longer time (typically, the duty cycle associated with this ON/OFF operation of the boost converter circuit U1 is no greater than about 0.01), thereby controlling and limiting the amount of current that is drawn from the battery. This ON/OFF action of U1 assures that the battery voltage, $V_{BAT}$, always remains sufficiently high to permit operation of all the critical circuits of the IEAD 100 (principally the circuits of the microcontroller U2), except the boost converter circuit U1.

In a preferred implementation, the microcontroller circuit U2 used in FIG. 21 comprises an MSP430G24521RSA 16 microcontroller, commercially available from Texas Instruments, or equivalent microcontroller The programmable current source circuit U3 comprises a LT3092 programmable current source commercially available form Linear Technology, or equivalents thereof. The sensor circuit U4 comprises an AS-M15SA-R magnetic sensor, commercially available from Murata, or equivalents thereof. And, the switch circuit U5 comprises an ADG1419BCPZ single pole double throw analog switch commercially available from Analog Devices, or equivalents thereof.

A further feature or enhancement provided by the circuit implementation depicted in FIG. 21 relates to removing, or at least minimizing, some undesirable leading edge transients that are seen in the output stimulus pulses generated by the circuitry of FIG. 21. The solution to remove or mitigate the occurrence of such leading edge transients is to insert an N-MOSFET transistor switch Q1 at the input terminal, IN, of the programmable current source circuit U3. This switch Q1 acts as a "cascode" stage that maintains a more constant voltage across the current source U3 as the output current and/or load resistance changes. Use of this N-MOSFET switch Q1 as depicted in FIG. 21 as a cascode stage advantageously reduces the transient leading edge of the stimulus pulse because the capacitance looking into Q1 is much less than is seen when looking into the current source circuit U3.

Yet an additional feature or enhancement provided by the circuitry of FIG. 21 is to address a delay that is seen when starting up the programmable current source circuit U3 when programmed to provide low pulse amplitudes, (e.g., less than about 3 mA). A typical current stimulus output for the IEAD is on the order of 15-25 mA. When a much smaller amplitude current stimulus is used, e.g., 1.5-3 mA, the control signal that defines this smaller amplitude pulse is significantly less than the one used to define the more typical stimulus amplitudes of 15-25 mA. Such a small control signal lengthens the delay between a trigger point and the leading edge of a stimulus pulse. This problem is addressed through use a Schottky diode D5 connected from an output port on the microcontroller circuit U2 to the input port, IN, of the current source circuit U3. This Schottky diode D5 is realized, for the embodiment shown in FIG. 21, using a BAT54XV2DKR diode, commercially available from Fairchild Semiconductor. This diode D5 is used to warm-up or "kick start" the circuit U3 when the pulse amplitude is low. Use of the diode D5 allows the microcontroller U2 to drive U3 directly at the start of the pulse, over the signal line labeled "KICKER" in FIG. 21, without significantly changing the pulse characteristics.

Use and Operation

With the implantable electroacupuncture device (IEAD) 100 in hand, the IEAD 100 is used most effectively to treat a specified disease or medical condition of the patent by first pre-setting stimulation parameters that the device will use during a stimulation session. FIG. 8 shows a timing waveform diagram illustrating the EA stimulation parameters used by the IEAD to generate EA stimulation pulses. As seen in FIG. 8, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is dictated or defined by the time period T3. The amplitude of the stimulus pulses is defined by the amplitude A1. This amplitude may be expressed in either voltage or current.

Turning next to FIG. 8A, a timing waveform diagram is shown that illustrates the manner in which the stimulation sessions are administered in accordance with a preferred stimulation regimen. FIG. 8A shows several stimulation sessions of duration T3, and how often the stimulation sessions occur. The stimulation regimen thus includes a time period T4 which sets the time period from the start of one stimulation session to the start of the next stimulation session. The time period T4 thus is the period of the stimulation session frequency, and the stimulation session frequency is equal to 1/T4.

In order to allow the applied stimulation to achieve its desired effect on the body tissue at the selected target stimulation site, an initialization period, typically no longer than two weeks, may be employed wherein the period of the stimulation session T4 may be varied. After the initialization period, the stimulation sessions are regularly applied to the patient using a fixed value of T4. For example, after the initialization period, the stimulation sessions may be applied to the patient no more than twice a week (i.e., T4=5,040 minutes), but no less than once every other week (i.e., T4=20, 160 minutes).

During the initialization period, the value of T4 can be varied, in accordance with one implementation, by employing a simple algorithm within the circuitry of the EA device changes the value of T4 in an appropriate manner. For example, at start up, the period T4 may be set to a minimum value, T4(min). Then, as time goes on, the value of T4 may be gradually increased until a desired value of T4, T4(final) is reached.

By way of example, during the initialization period, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example, a first 30 minute stimulation session could be delivered after 1 day. The second 30 minute session could be delivered after 2 days. The third 30 minute session could be delivered after 4 days. Finally, the fourth 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. For example, should the first session be aborted by a magnet application, the device reverts to a Shelf Mode. In this way, the first session is always a triggered session that occurs in the clinician setting.

The programmed values of amplitude and place in a session table are saved in non-volatile memory when they change. This avoids a resetting of the therapy schedule and need to reprogram the amplitude in the event of a device reset.

By way of example, one set of parameters that could be used to define a stimulation regimen is:
T1=0.5 milliseconds
T2=500 milliseconds
T3=30 minutes
T4=7 days (10,080 minutes)
A1=15 volts (across 1 kOhm), or 15 milliamperes (mA)

It is to be emphasized that the values shown above for the stimulation regimen are representative of only one preferred stimulation regimen that could be used.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired stimulation site (e.g., acupoint), but it also limits the frequency and duration of stimulation sessions.

Limiting the frequency and duration of the stimulation sessions is a key aspect of Applicant's invention because it recognizes that some treatments, such as treating high blood pressure, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce a sustained therapeutic effect. Thus, Applicant has based its treatment regimen on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit U2, the IEAD 100 needs to be implanted. Implantation is usually a simple procedure, and is described above in connection, e.g., with the description of FIGS. 10 and 11.

Figure 22:
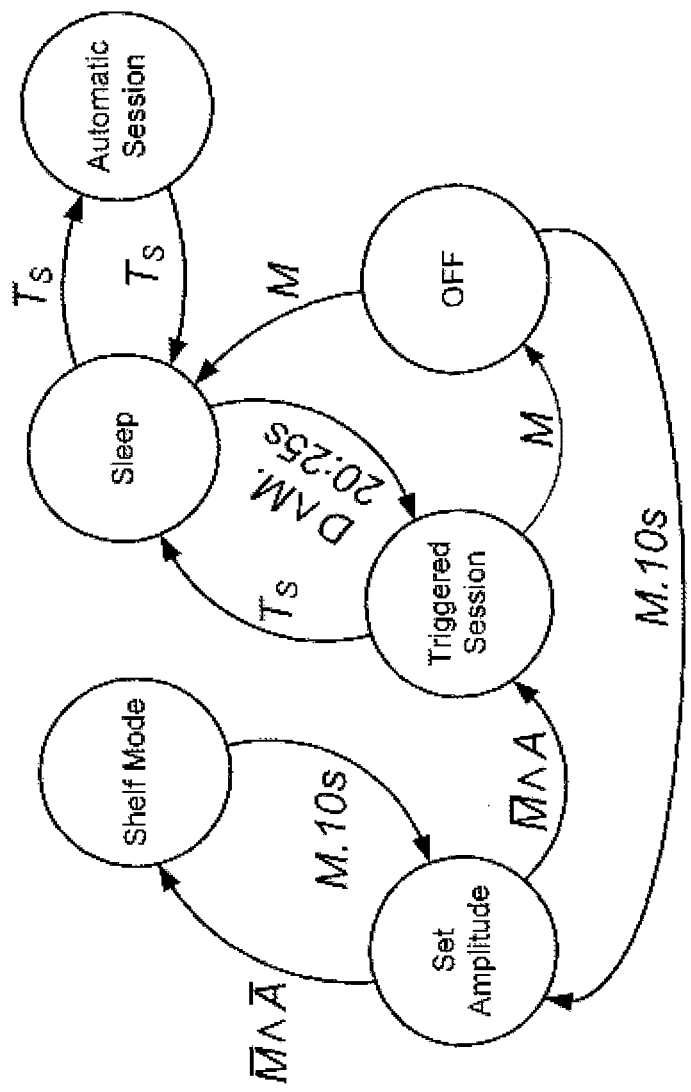
FIG. 22 shows a state diagram that depicts the various states the IEAD may assume as controlled by an external magnet.

After implantation, the IEAD must be turned ON, and otherwise controlled, so that the desired stimulation regimen or stimulation paradigm may be carried out. In one preferred embodiment, control of the IEAD after implantation, as well as anytime after the housing of the IEAD has been hermetically sealed, is performed as shown in the state diagram of FIG. 22. Each circle shown in FIG. 22 represents an operating "state" of the micro-controller U2 (FIG. 21). As seen in FIG. 22, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M} \wedge A$), the device continues into the "Triggered Session" so the patient receives the initial therapy. If the magnet is removed during "Set Amplitude" while the amplitude is zero ($\overline{M} \wedge \overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 22 as a function of externally-generated magnetic control commands, or other externally-generated command signals, is the micro-controller U2 (FIG. 21). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C, attached hereto, and incorporated by reference herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. A self-contained implantable electroacupuncture device (IEAD) for treating a specified medical condition of a patient through application of electroacupuncture (EA) stimulation pulses applied substantially at or near a specified acupoint, comprising:
    a rigid, coin-shaped housing having a thickness of no greater than about 2.5 mm and a diameter no greater than about 25 mm;
    at least one cathodic electrode and at least one anodic electrode formed in a prescribed configuration as an integral part of at least one outside surface of the housing;
    stimulation circuitry residing inside the housing and electrically coupled to the at least one cathodic and at least one anodic electrodes, wherein the stimulation circuitry generates EA stimulation pulses that are delivered to body tissue through the at least one cathodic and at least one anodic electrodes in accordance with a prescribed stimulation regimen, wherein said stimulation regimen defines the duration and rate at which a stimulation session is applied to the patient, said stimulation regimen requiring that the stimulation session have a duration of T3 minutes, wherein T3 is at least 10 minutes, and a rate of occurrence of once every T4 minutes, wherein the ratio of T3/T4 is no greater than 0.05, and wherein during each stimulation session EA stimulation pulses having one or more specified widths and amplitudes are generated at one or more specified rates; and
    a coin-cell type primary battery residing inside the housing that provides the operating power for the stimulation circuitry, wherein the primary battery has an internal impedance that is greater than 5 ohms;
    wherein the IEAD is leadless and the IEAD housing is hermetically-sealed, and the coin-cell primary battery has sufficient capacity to power the operation of the IEAD in accordance with the prescribed stimulation regimen for at least two years without any further action needed on the part of the patient or other medical personnel; and
    wherein the at least one cathodic electrode is located on a top or bottom surface of the housing and positioned no closer than 5 mm from the closest edge of the nearest at least one anodic electrode, wherein at least one of the cathodic or anodic electrodes comprises an annular or circumscribing electrode that surrounds or encompasses the other at least one cathodic or anodic electrodes, and wherein the total surface area of the at least one cathodic electrode is no smaller than about 0.5 mm$^2$, and wherein the positioning and surface area of the at least one cathodic electrode is selected to allow a desired current density to flow through the electrode surface area without causing electrode corrosion or current shunting.

2. The IEAD of claim 1, wherein the at least one cathodic electrode comprises a first cathodic electrode located on a top surface of the housing and a second cathodic electrode located on a bottom surface of the housing, and wherein the stimulation circuitry includes switching circuitry that selectively activates (i) only the first cathodic electrode, or (ii) only the second cathodic electrode, or (iii) both the first and second cathodic electrodes when the stimulation pulses are delivered to the body tissue in accordance with the prescribed stimulation regimen.

3. The IEAD of claim 2, wherein the at least one anodic electrode is formed as a ring electrode residing substantially around a perimeter edge of the housing.

4. The IEAD of claim 3, wherein the first and second cathodic electrodes each comprise multiple small cathodic electrodes distributed over the top and bottom surface areas of the housing in accordance with a prescribed pattern.

5. The IEAD of claim 4 wherein the at least one anodic electrode comprises multiple small anodic electrodes distributed around the perimeter edge of the housing.

6. The IEAD of claim 5 wherein the stimulation circuitry includes additional cathodic switching circuitry that selectively activates only a desired grouping of the first and second cathodic electrodes, wherein the location of the body tissue receiving the stimulation pulses may be selected by controlling which groups of electrodes are activated and which are not activated, wherein an activated electrode comprises an electrode that is turned ON by the switching circuitry so that an electrical current may flow through the electrode, and a non-activated electrode comprises an electrode that is turned OFF by the switching circuitry so as to prevent electrical current from flowing through the electrode.

7. The IEAD of claim 1 wherein the housing has a maximum linear dimension no greater than about 25 mm in a first plane orthogonal to a second plane wherein the thickness of the housing is measured, and wherein the at least one cathodic electrode comprises a single cathodic electrode located in the center of a bottom surface of the housing, the bottom surface comprising that surface of the housing adapted to face towards a desired target tissue location whereat EA stimulation pulses are to be applied.

8. The IEAD of claim 1 wherein the single cathodic electrode is segmented into a central electrode and a plurality of concentric ring electrodes surrounding the central electrode.

* * * * *